United States Patent
Hiemer et al.

(10) Patent No.: US 11,628,986 B2
(45) Date of Patent: Apr. 18, 2023

(54) DEVICE FOR DISCHARGING A POURABLE SUBSTANCE

(71) Applicants: Andreas Hiemer, Papenburg (DE); Alberto C. Sögaro, Bad Homburg (DE); Sebastian Seitz, Dürrwangen (DE)

(72) Inventors: Andreas Hiemer, Papenburg (DE); Alberto C. Sögaro, Bad Homburg (DE); Sebastian Seitz, Dürrwangen (DE)

( * ) Notice: Subject to any disclaimer, the term of this patent is extended or adjusted under 35 U.S.C. 154(b) by 378 days.

(21) Appl. No.: 16/770,017

(22) PCT Filed: Dec. 4, 2018

(86) PCT No.: PCT/EP2018/083527
§ 371 (c)(1),
(2) Date: Jun. 4, 2020

(87) PCT Pub. No.: WO2019/110605
PCT Pub. Date: Jun. 13, 2019

(65) Prior Publication Data
US 2020/0385181 A1    Dec. 10, 2020

(30) Foreign Application Priority Data

Dec. 5, 2017 (DE) .................. 10 2017 128 918.6
Jun. 26, 2018 (DE) .................. 10 2018 115 344.9

(51) Int. Cl.
B65D 47/36    (2006.01)
A61J 1/06     (2006.01)
A61J 7/00     (2006.01)

(52) U.S. Cl.
CPC .............. *B65D 47/36* (2013.01); *A61J 1/065* (2013.01); *A61J 7/0023* (2013.01)

(58) Field of Classification Search
CPC .......... B65D 47/36; A61J 1/065; A61J 7/0023
(Continued)

(56) References Cited

U.S. PATENT DOCUMENTS 1,822,566 A * 9/1931 Davies ................ A61M 35/006
                                                      604/3
2,517,604 A * 8/1950 Smith ................... A61J 1/065
                                                      215/901

(Continued)

FOREIGN PATENT DOCUMENTS

FR    2610520 A1   8/1988
WO    9406690 A1   3/1994

(Continued)

OTHER PUBLICATIONS

PCT International Search Report and Written Opinion, PCT/EP2018/083527, dated Apr. 5, 2019, 20 pages.

*Primary Examiner* — Frederick C Nicolas
*Assistant Examiner* — Michael J. Melaragno
(74) *Attorney, Agent, or Firm* — Quarles & Brady LLP

(57) ABSTRACT

A device for discharging a flowable substance, in particular for applying a medical substance, a pharmaceutical substance, a food supplement or a cosmetics, includes an activation mechanism and a body which has a discharge opening at a first end and forms a containing space in which a frangible capsule is disposed. The capsule has two ends each having a first and a second tip and at least one of the two tips can be snapped off by actuating the activation mechanism so that the flowable substance is discharged.

16 Claims, 24 Drawing Sheets

(58) Field of Classification Search
USPC .......................................................... 222/81
See application file for complete search history.

(56) References Cited

U.S. PATENT DOCUMENTS

| | | | | |
|---|---|---|---|---|
| 3,068,154 A * | 12/1962 | Majors | ................... | C12M 23/34 |
| | | | | 435/840 |
| 3,152,352 A * | 10/1964 | Kosik, Jr. | ............. | B60S 1/0483 |
| | | | | 401/199 |
| 3,220,413 A * | 11/1965 | Sunnen | ................... | A61F 13/26 |
| | | | | 604/311 |
| 3,614,245 A * | 10/1971 | Schwartzman | ..... | A61M 35/006 |
| | | | | 604/3 |
| 3,924,623 A * | 12/1975 | Avery | ................. | A61M 35/006 |
| | | | | 604/3 |
| 3,964,643 A * | 6/1976 | Morane | .............. | B65D 81/3222 |
| | | | | 222/541.6 |
| 4,572,689 A * | 2/1986 | Chernack | ............ | A45D 34/042 |
| | | | | 401/15 |
| 5,052,588 A * | 10/1991 | Schlosser | .......... | A61M 5/31513 |
| | | | | 222/541.6 |
| 6,039,488 A * | 3/2000 | Krawczyk | ........... | A01M 31/008 |
| | | | | 401/199 |
| 6,343,717 B1 * | 2/2002 | Zhang | .................... | A61J 1/065 |
| | | | | 222/541.6 |
| 6,595,940 B1 * | 7/2003 | D'Alessio | ................. | A61P 1/02 |
| | | | | 604/3 |
| 7,004,657 B2 * | 2/2006 | Frazier | ............... | A46B 11/0003 |
| | | | | 401/133 |
| 7,032,590 B2 * | 4/2006 | Loeffler | .............. | A61M 15/009 |
| | | | | 206/532 |
| 7,726,519 B2 * | 6/2010 | Heldt | ..................... | B05B 11/02 |
| | | | | 222/326 |
| 8,631,941 B2 * | 1/2014 | Fazzolari | ............ | A61M 35/003 |
| | | | | 206/532 |
| 10,017,316 B2 * | 7/2018 | May | ....................... | B65D 11/20 |
| 10,442,598 B2 * | 10/2019 | May | ................... | B65D 81/3277 |
| 11,241,709 B1 * | 2/2022 | May | ...................... | A61B 90/80 |
| 2002/0076255 A1 * | 6/2002 | Hoang | ................ | A61M 35/006 |
| | | | | 401/133 |
| 2005/0072442 A1 * | 4/2005 | Licari | ...................... | A61Q 5/10 |
| | | | | 401/196 |
| 2005/0111900 A1 * | 5/2005 | Fazzolari | ............... | B65D 85/42 |
| | | | | 401/132 |
| 2006/0049203 A1 * | 3/2006 | Boone | .............. | A61B 17/00491 |
| | | | | 222/80 |
| 2006/0108385 A1 * | 5/2006 | Zahn | ....................... | A61J 1/067 |
| | | | | 222/541.9 |
| 2006/0113318 A1 * | 6/2006 | May | .................... | A45D 34/04 |
| | | | | 222/94 |
| 2009/0152295 A1 * | 6/2009 | May | ....................... | B65D 47/42 |
| | | | | 222/129 |
| 2009/0152296 A1 * | 6/2009 | May | .................. | B05C 17/00559 |
| | | | | 222/145.5 |
| 2011/0284583 A1 * | 11/2011 | Fazzolari | ............... | A45D 34/04 |
| | | | | 206/530 |
| 2014/0003858 A1 * | 1/2014 | Frazier | .................... | B05C 17/00 |
| | | | | 401/133 |
| 2015/0203275 A1 * | 7/2015 | May | .................... | B65D 81/3272 |
| | | | | 206/219 |
| 2016/0075168 A1 * | 3/2016 | Fehlmann | ............. | B43K 8/024 |
| | | | | 401/133 |
| 2018/0002098 A1 * | 1/2018 | May | .................... | B65D 81/3277 |
| 2018/0264507 A1 * | 9/2018 | Hiemer | ................ | B05C 17/0126 |
| 2020/0385181 A1 * | 12/2020 | Hiemer | ................ | A61J 7/0023 |
| 2021/0138214 A1 * | 5/2021 | Davidson | ............ | A61K 31/343 |
| 2022/0112022 A1 * | 4/2022 | May | ....................... | B65D 35/28 |

FOREIGN PATENT DOCUMENTS

| | | | | |
|---|---|---|---|---|
| WO | | 9909932 A1 | 3/1999 | |
| WO | | 2015042021 A1 | 3/2015 | |
| WO | WO-2019110605 A1 * | 6/2019 | ............. | A61J 1/065 |
| WO | WO-2019219130 A1 * | 11/2019 | ............. | A61M 5/24 |
| WO | WO-2021257687 A1 * | 12/2021 | | |

* cited by examiner

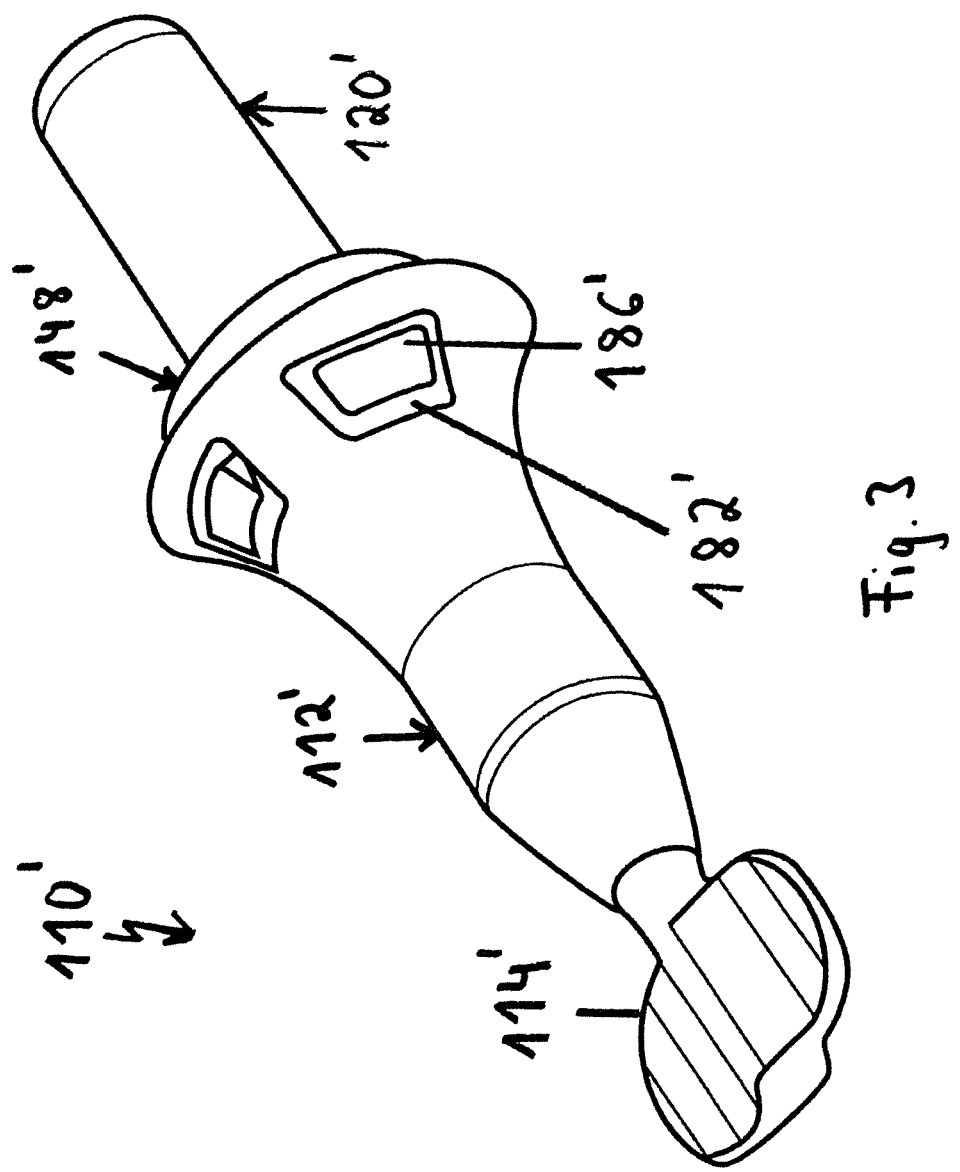

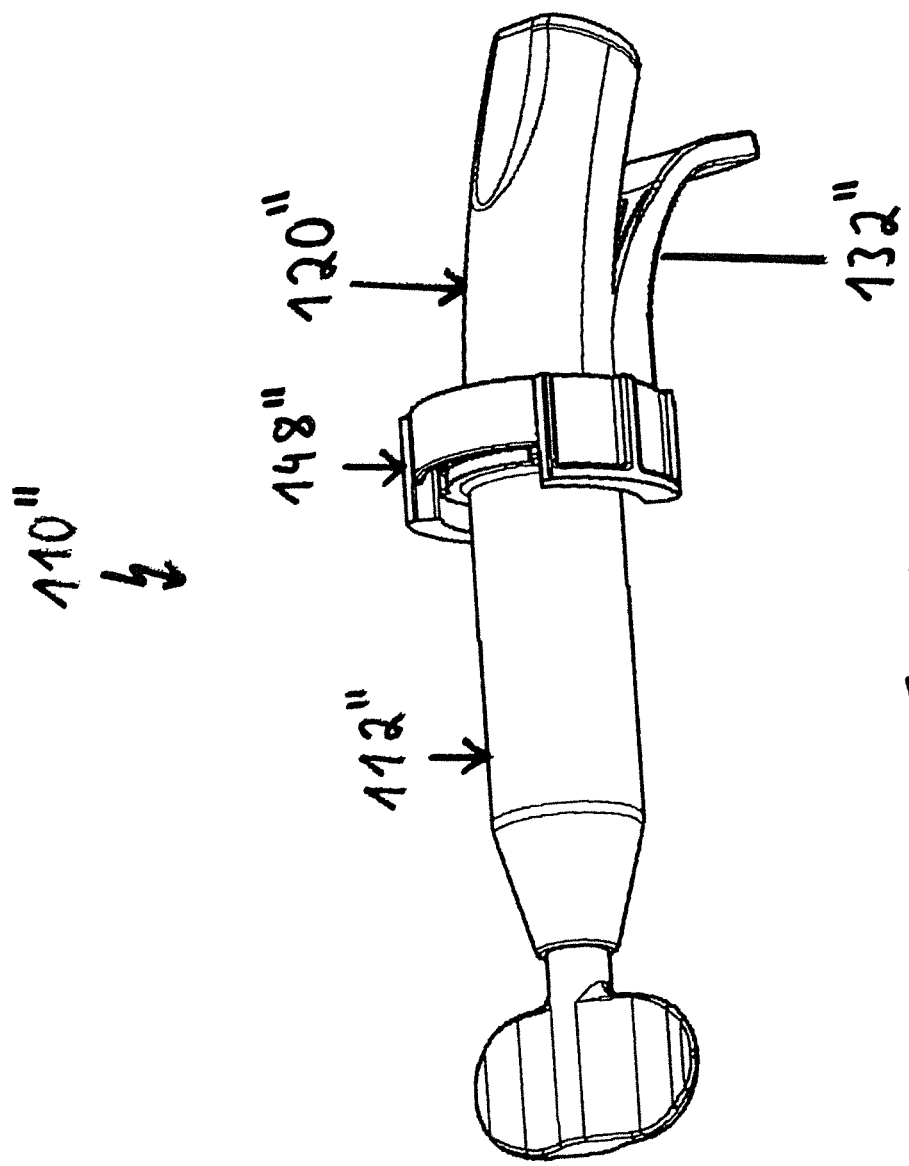

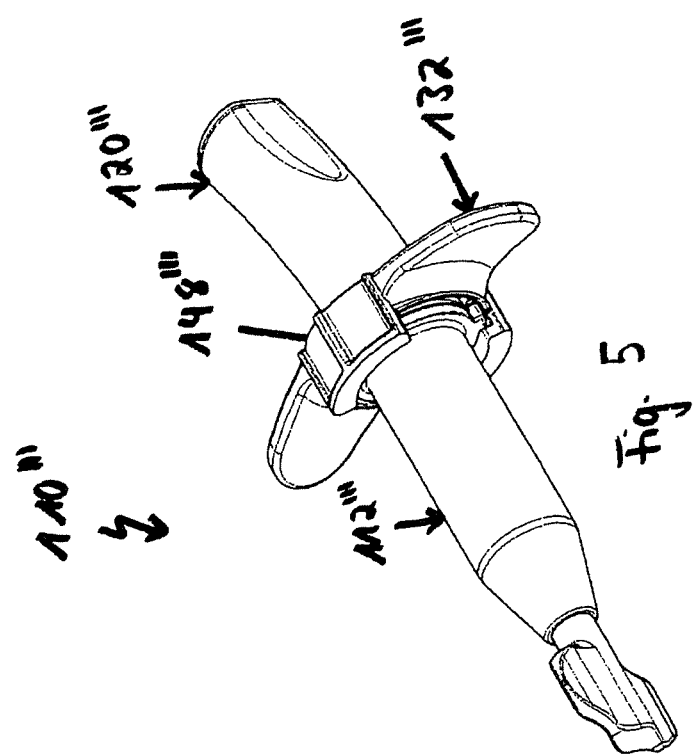

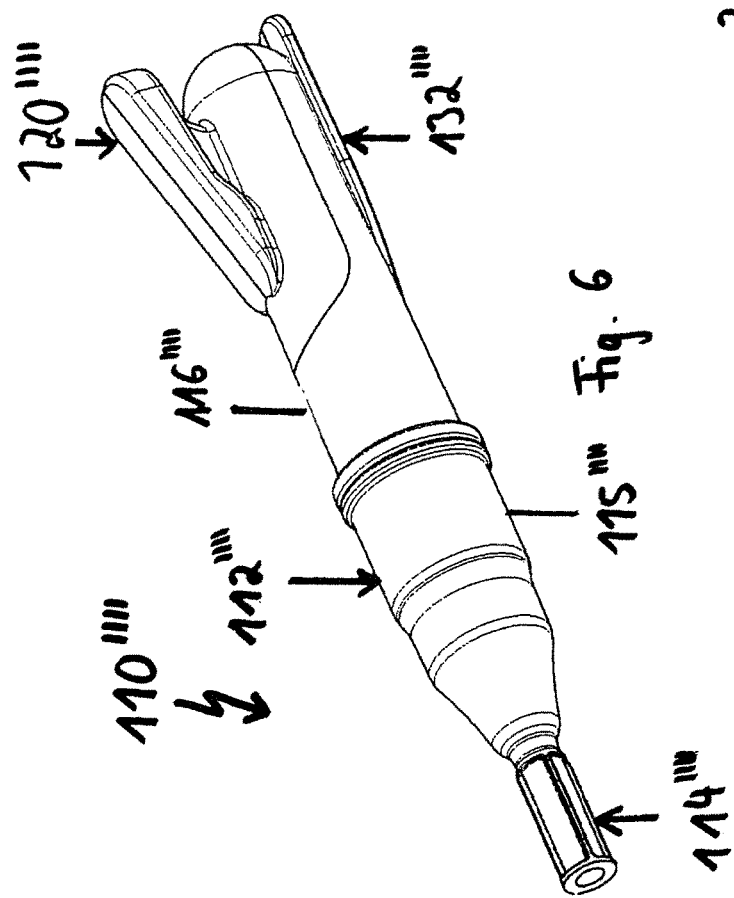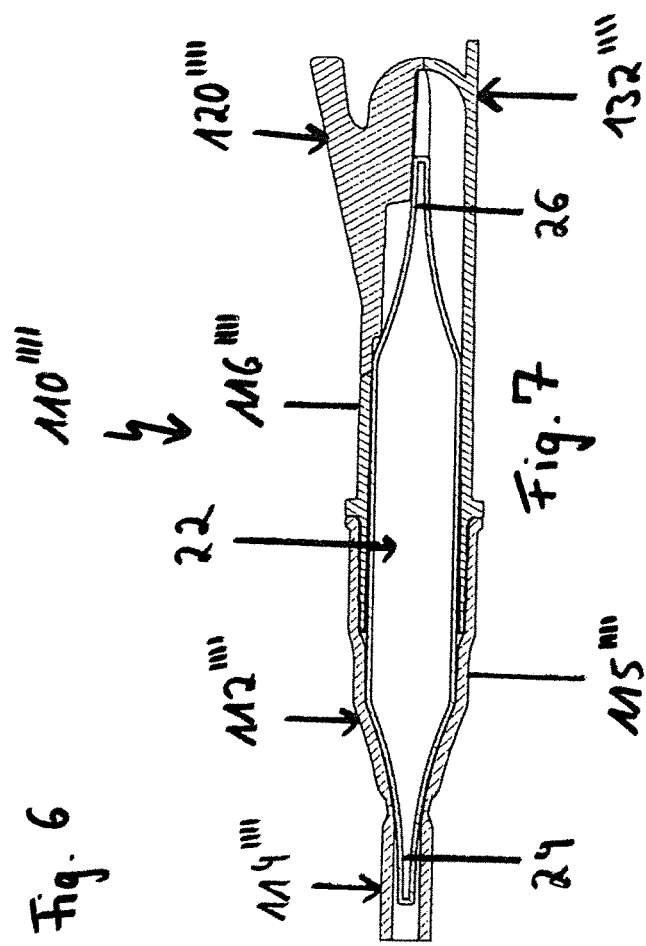

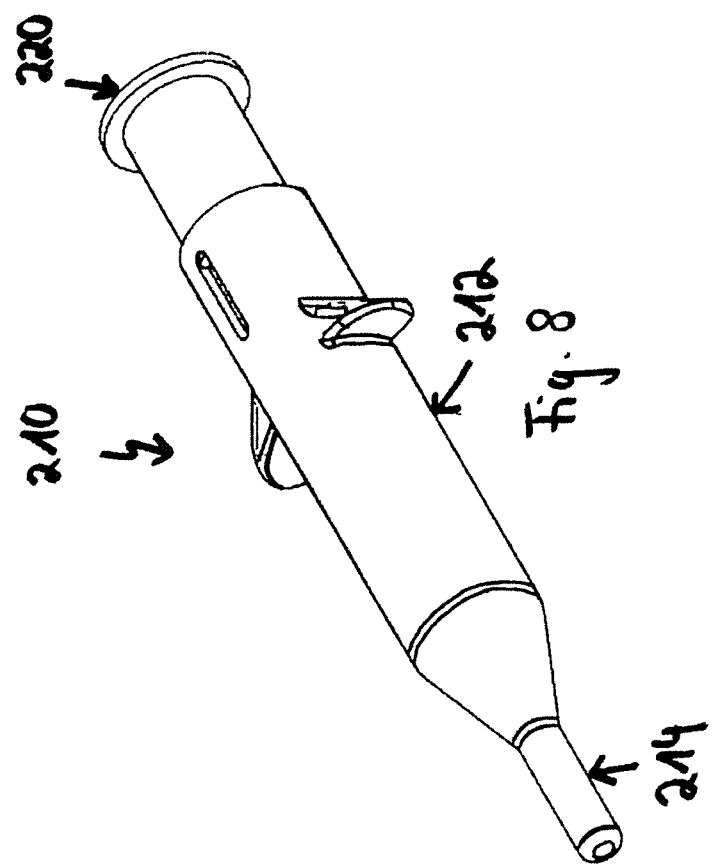

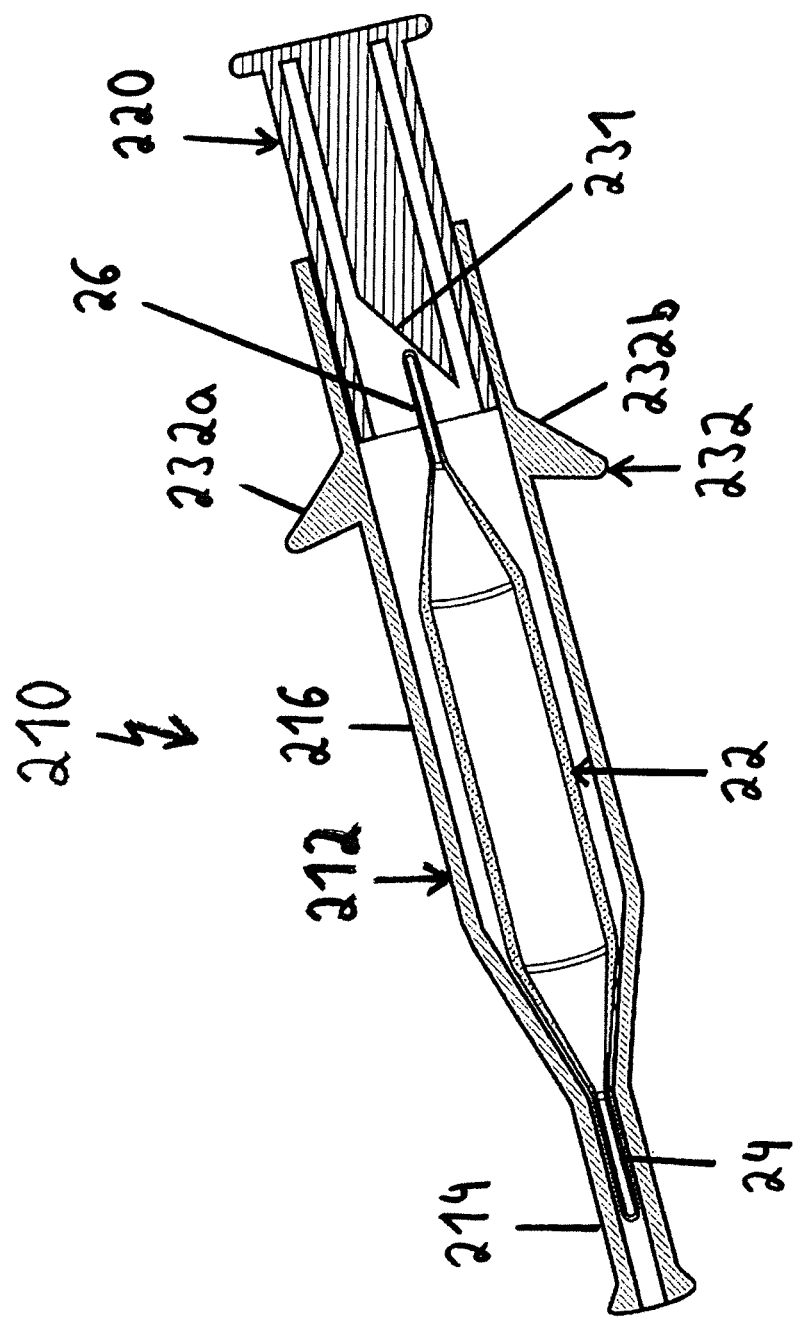

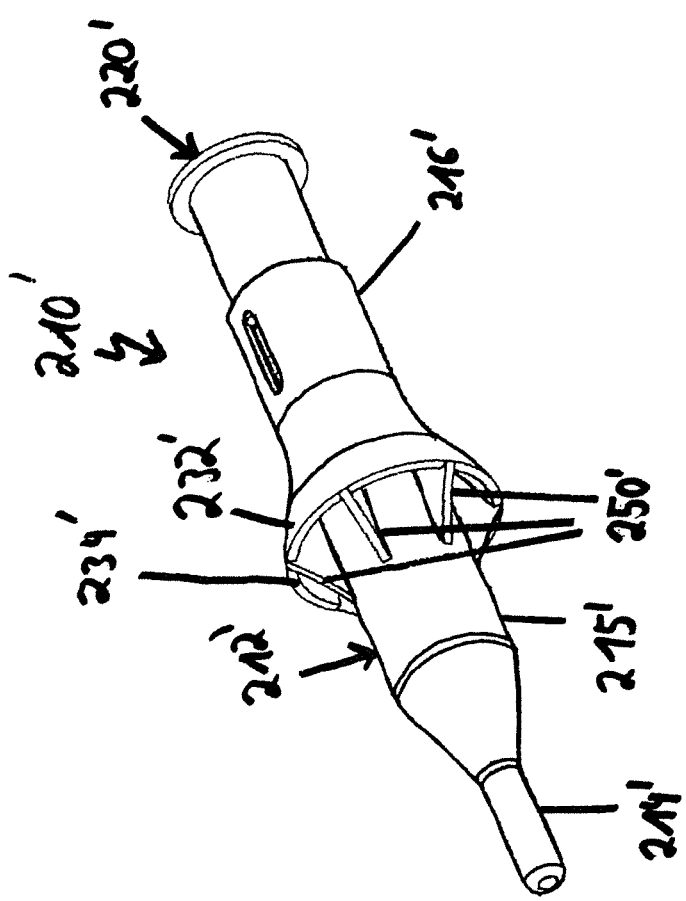

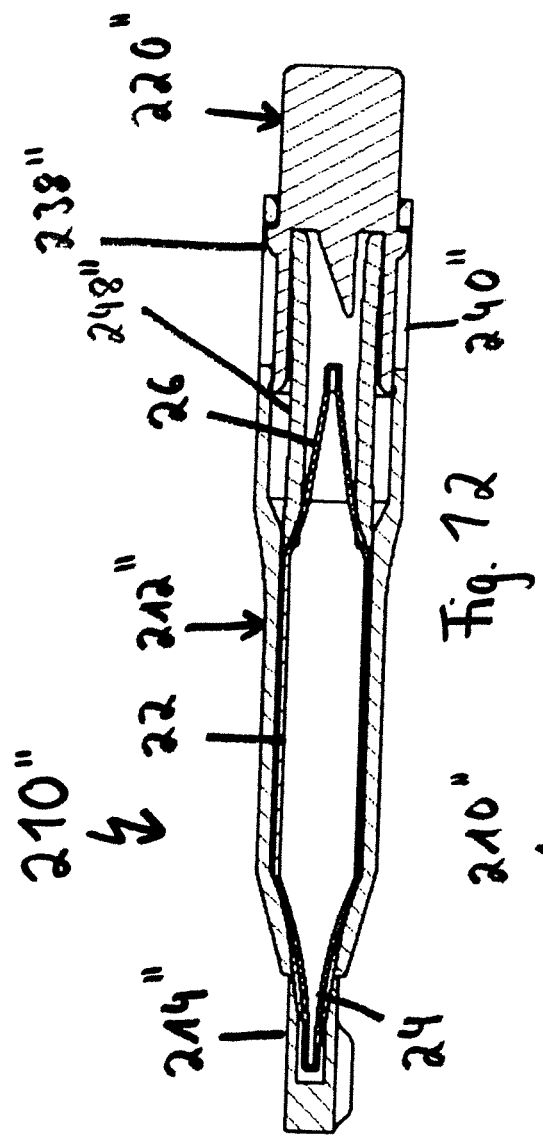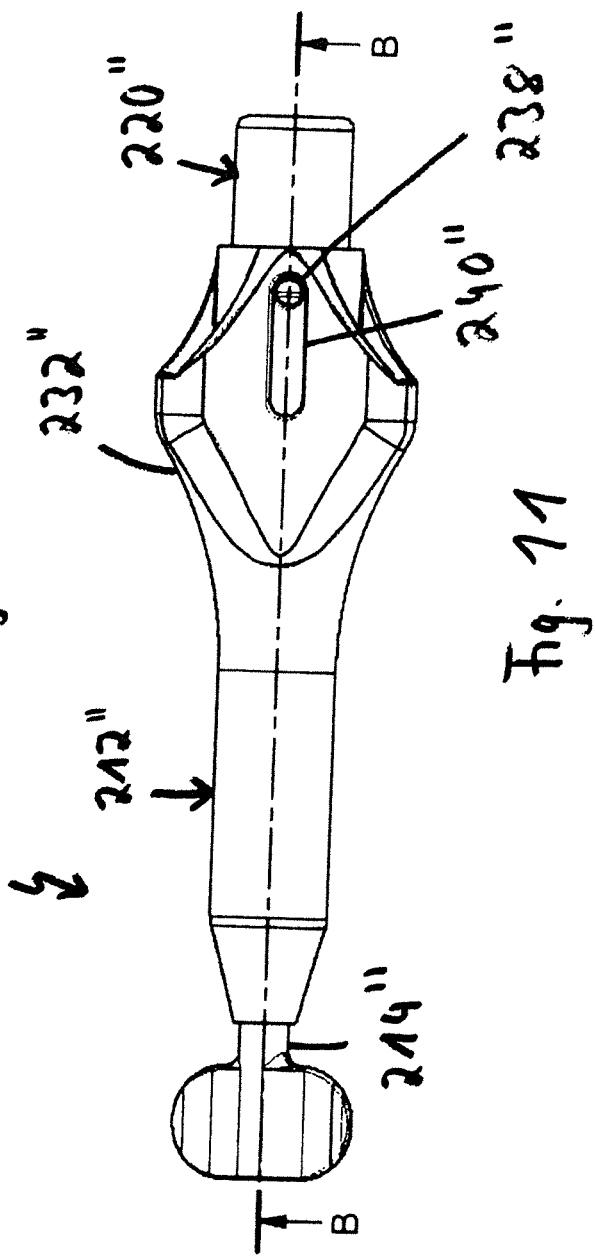

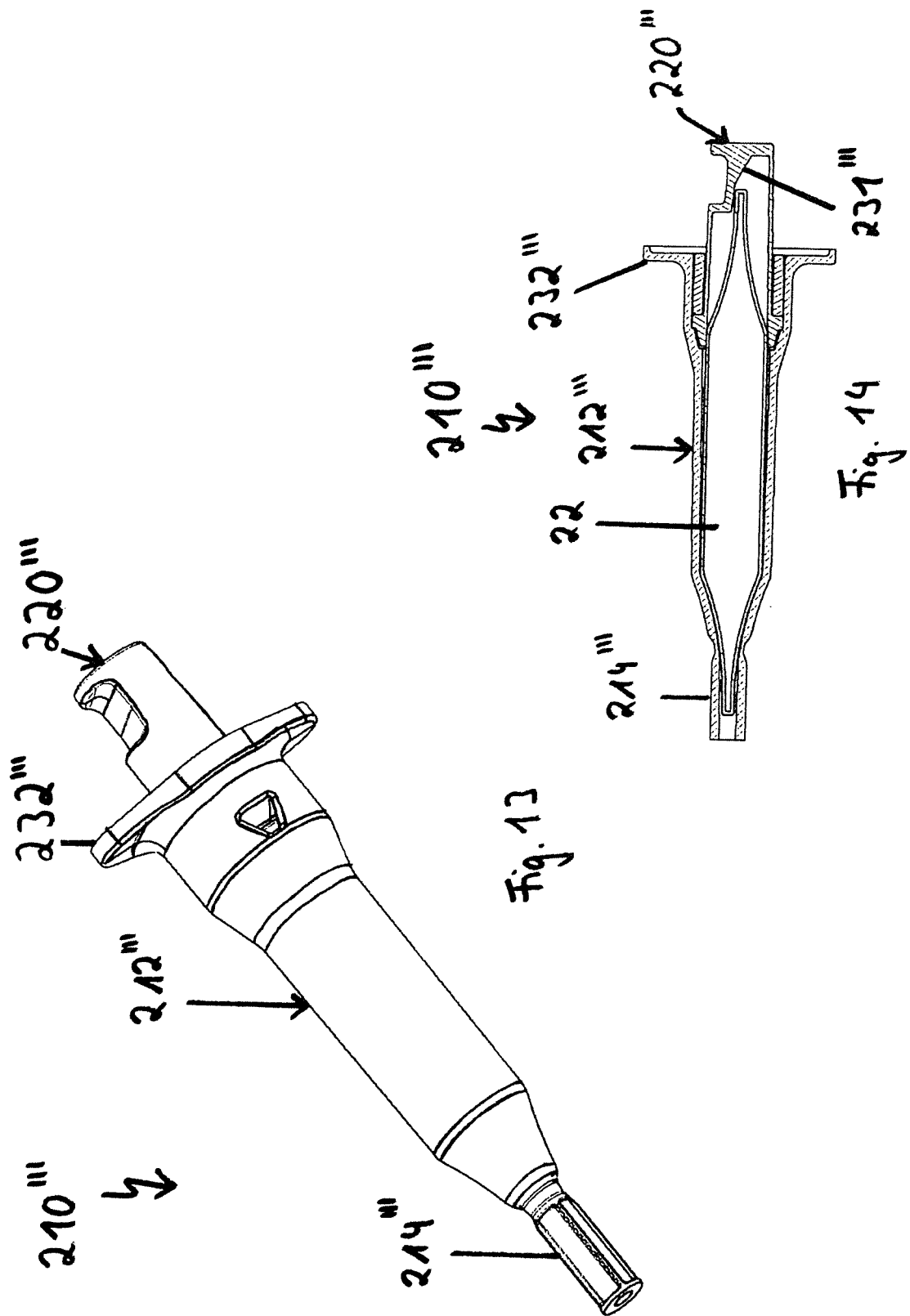

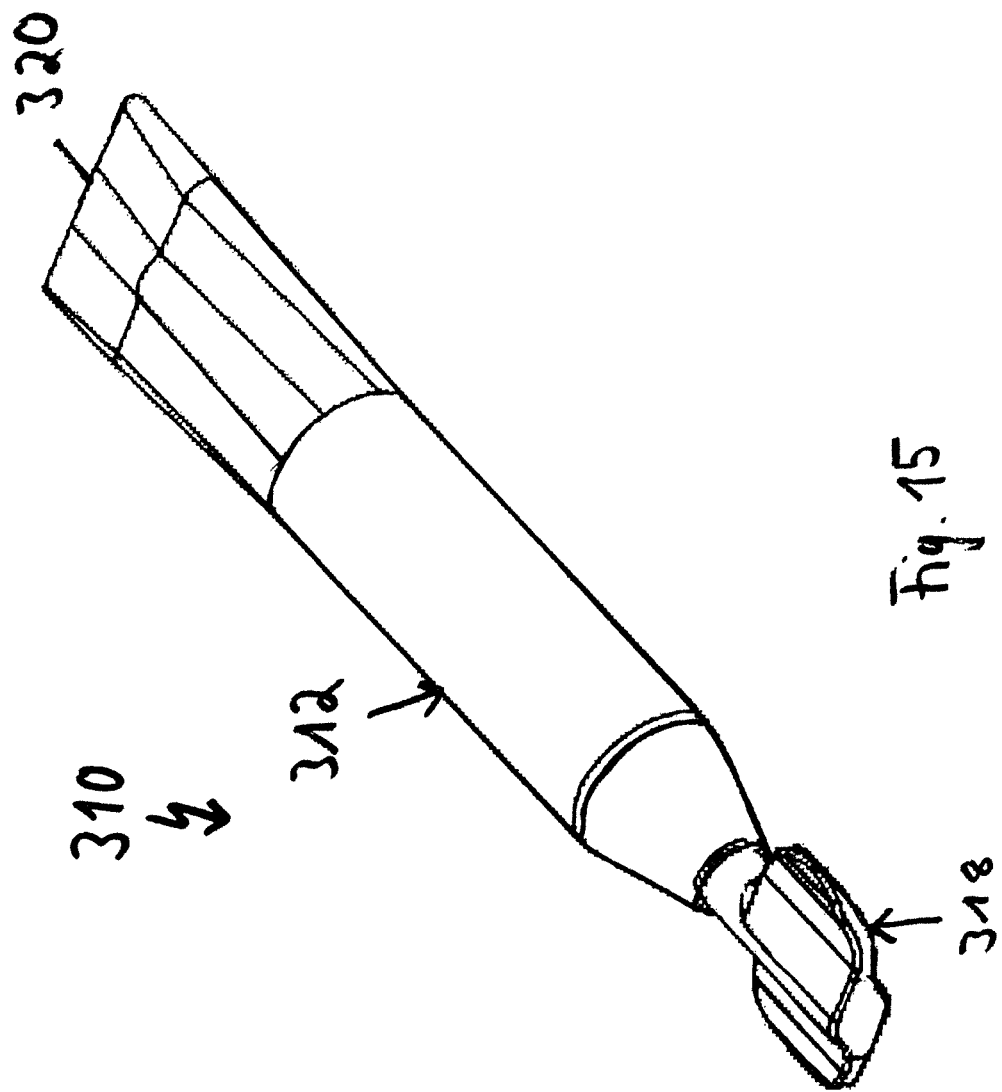

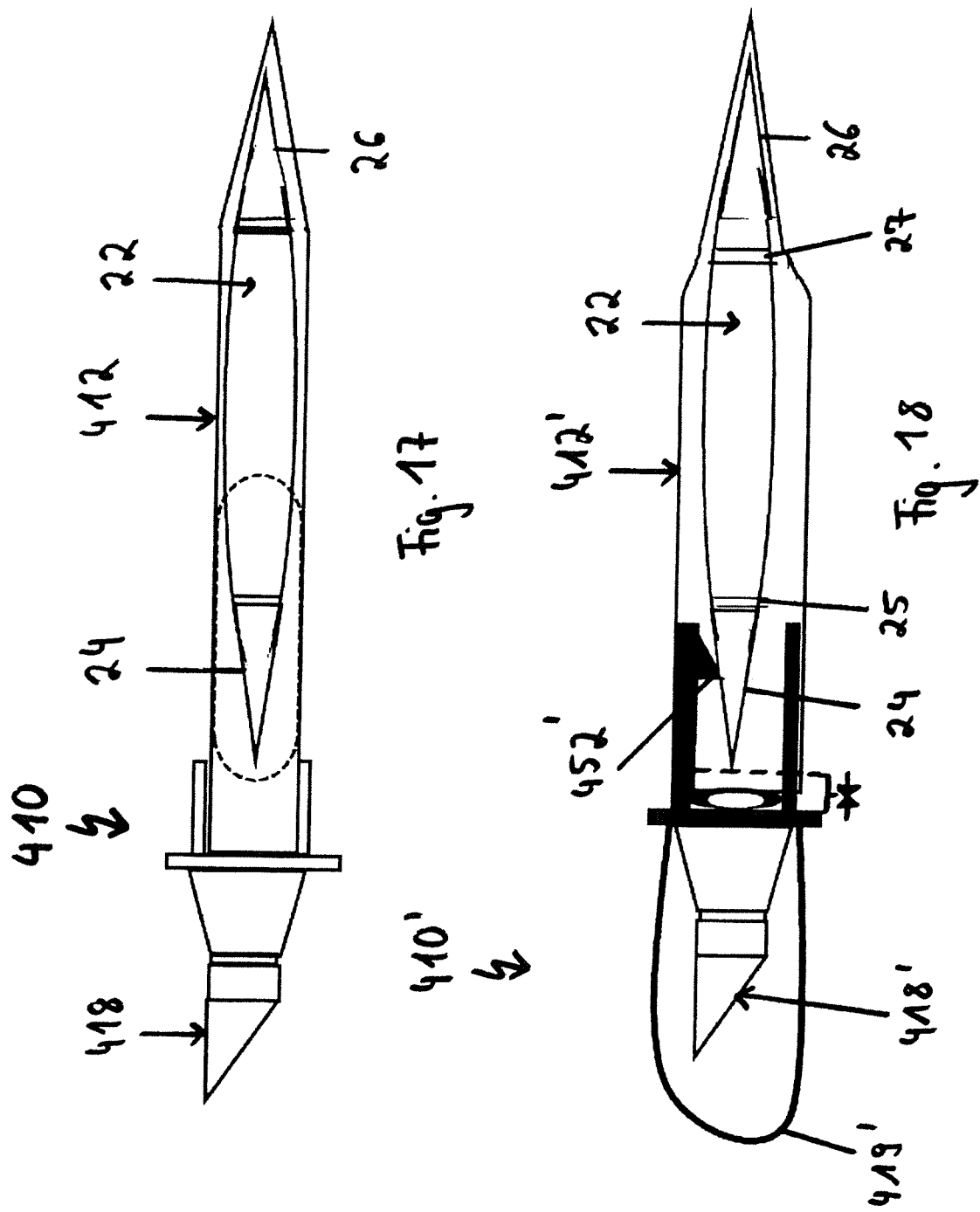

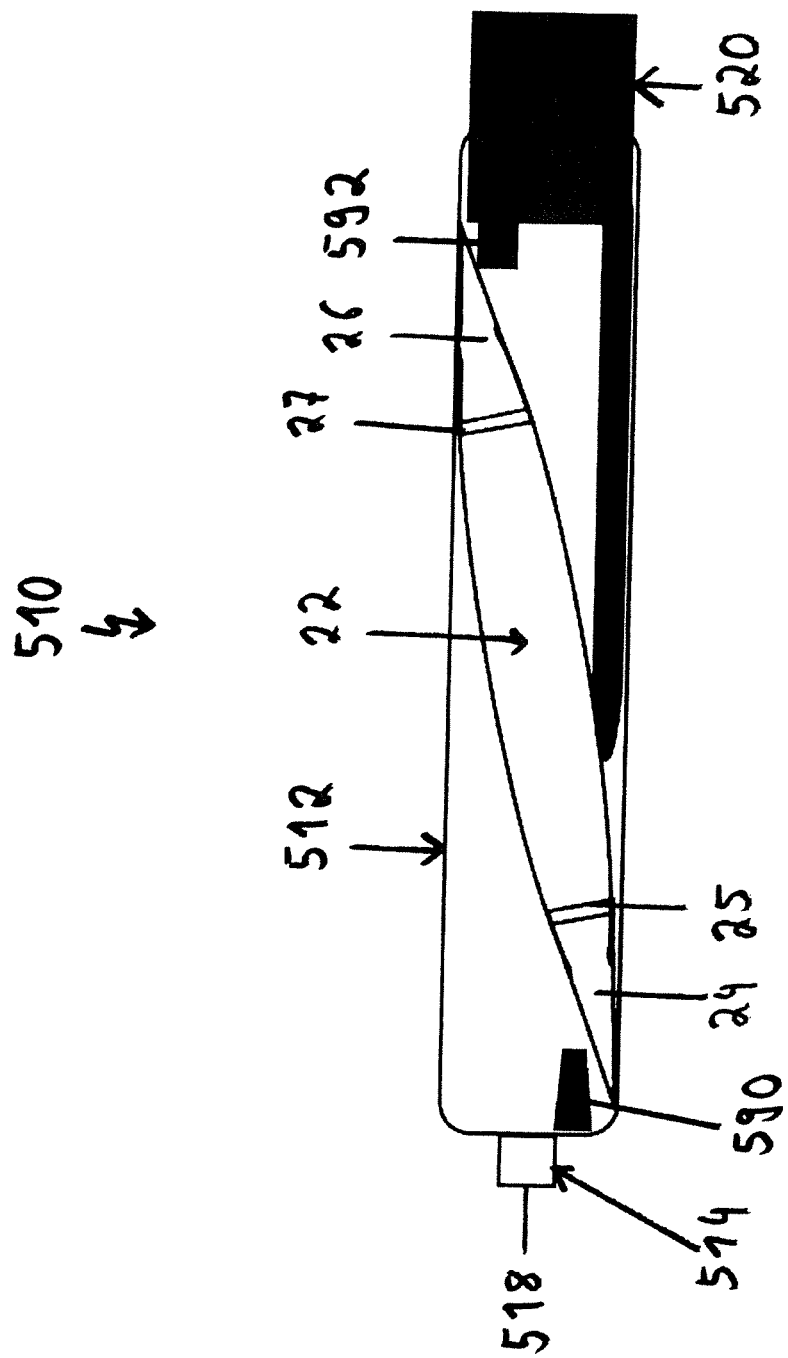

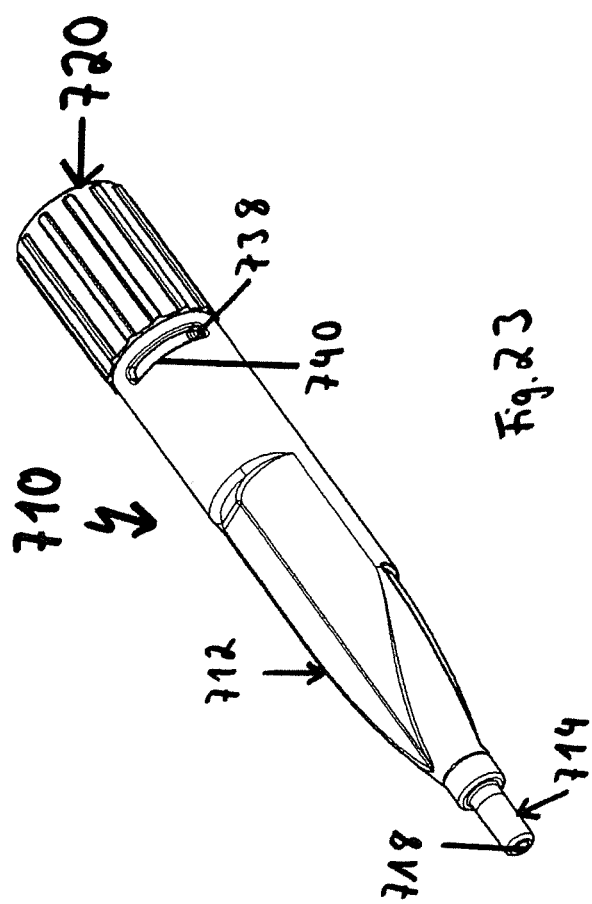

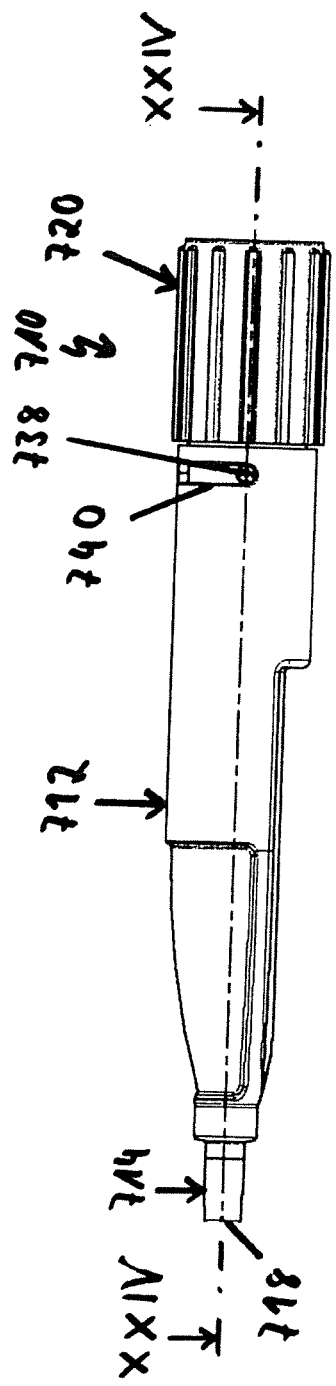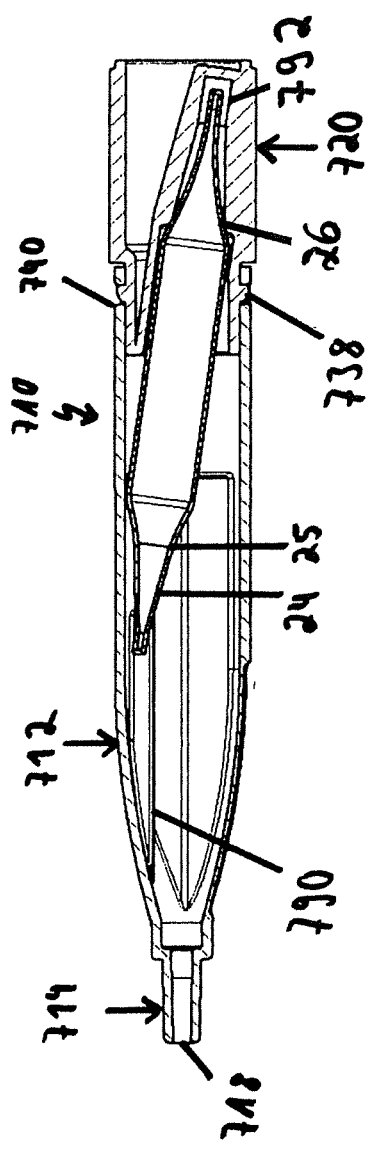

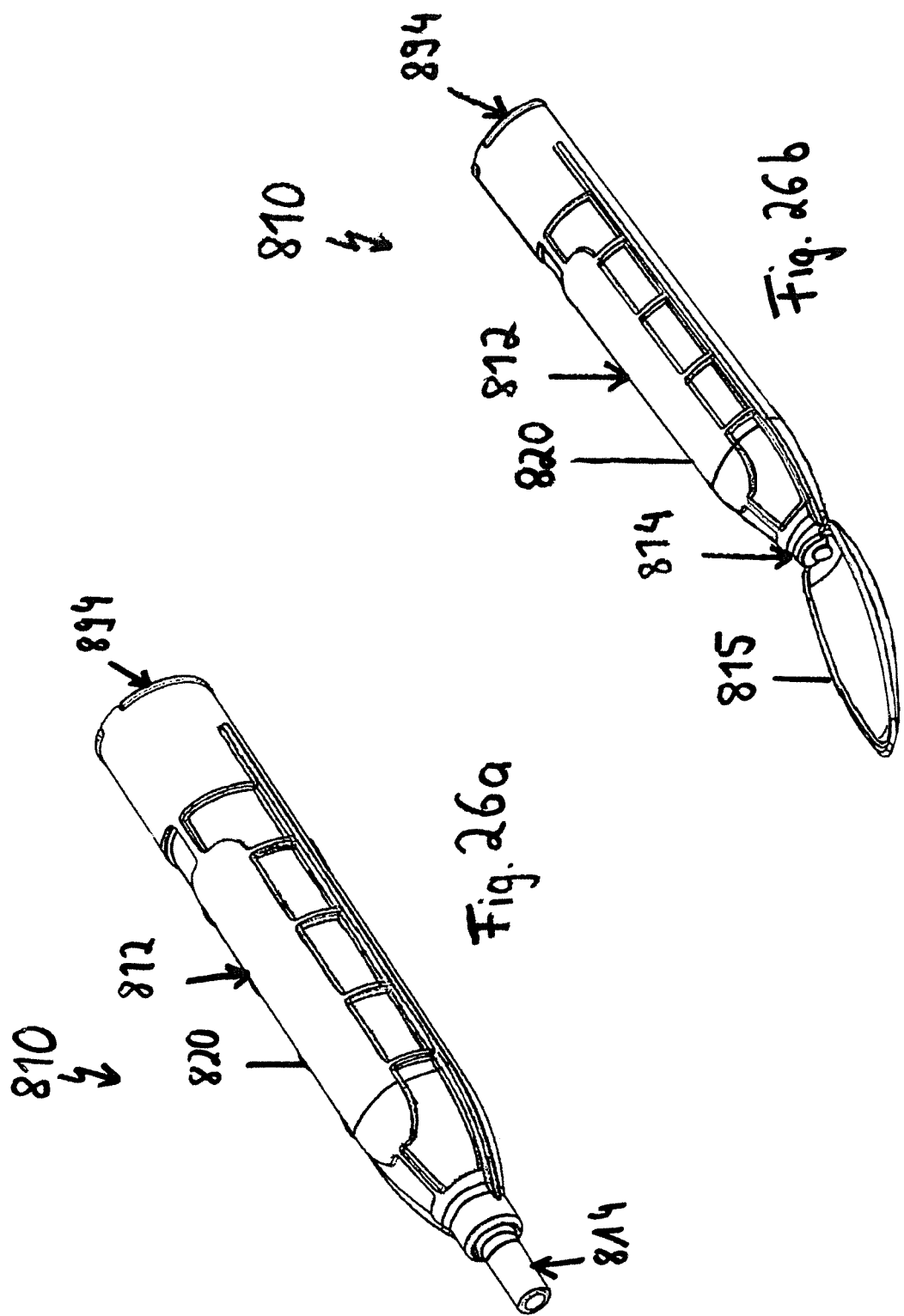

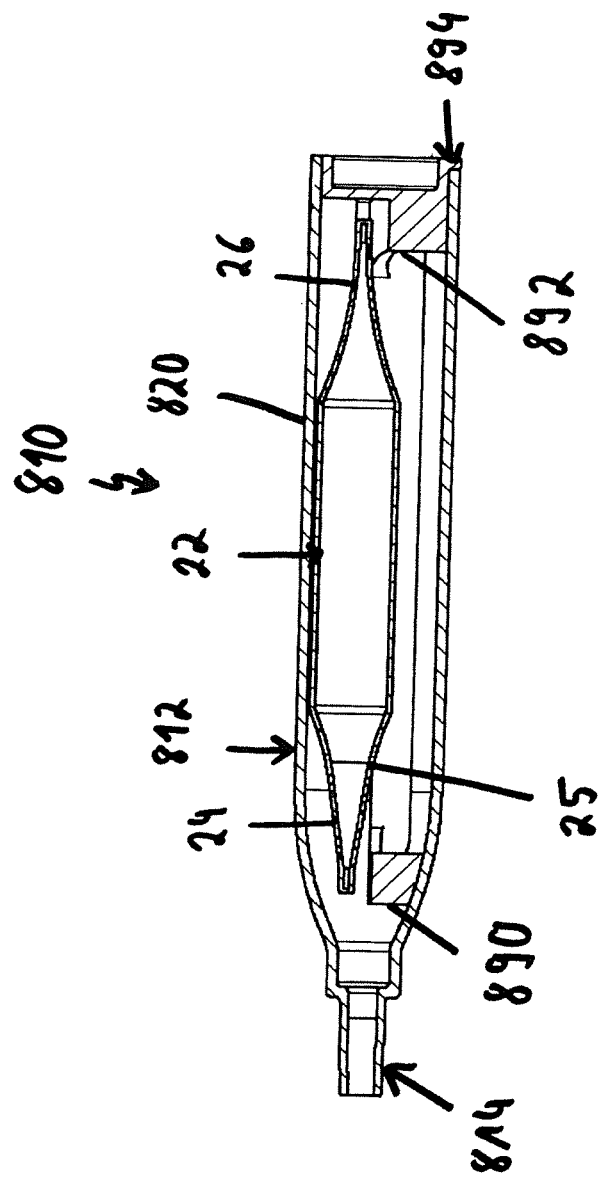

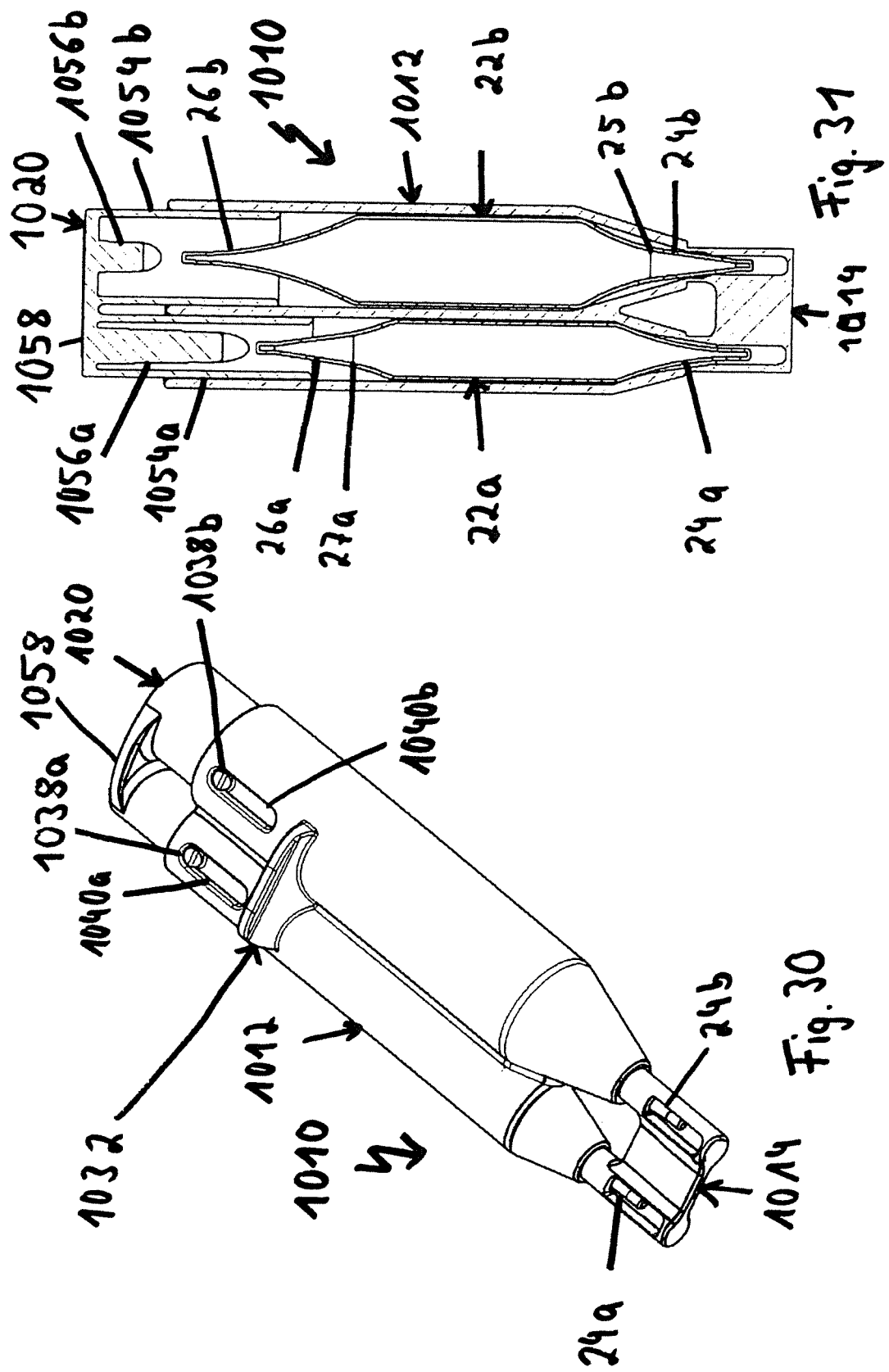

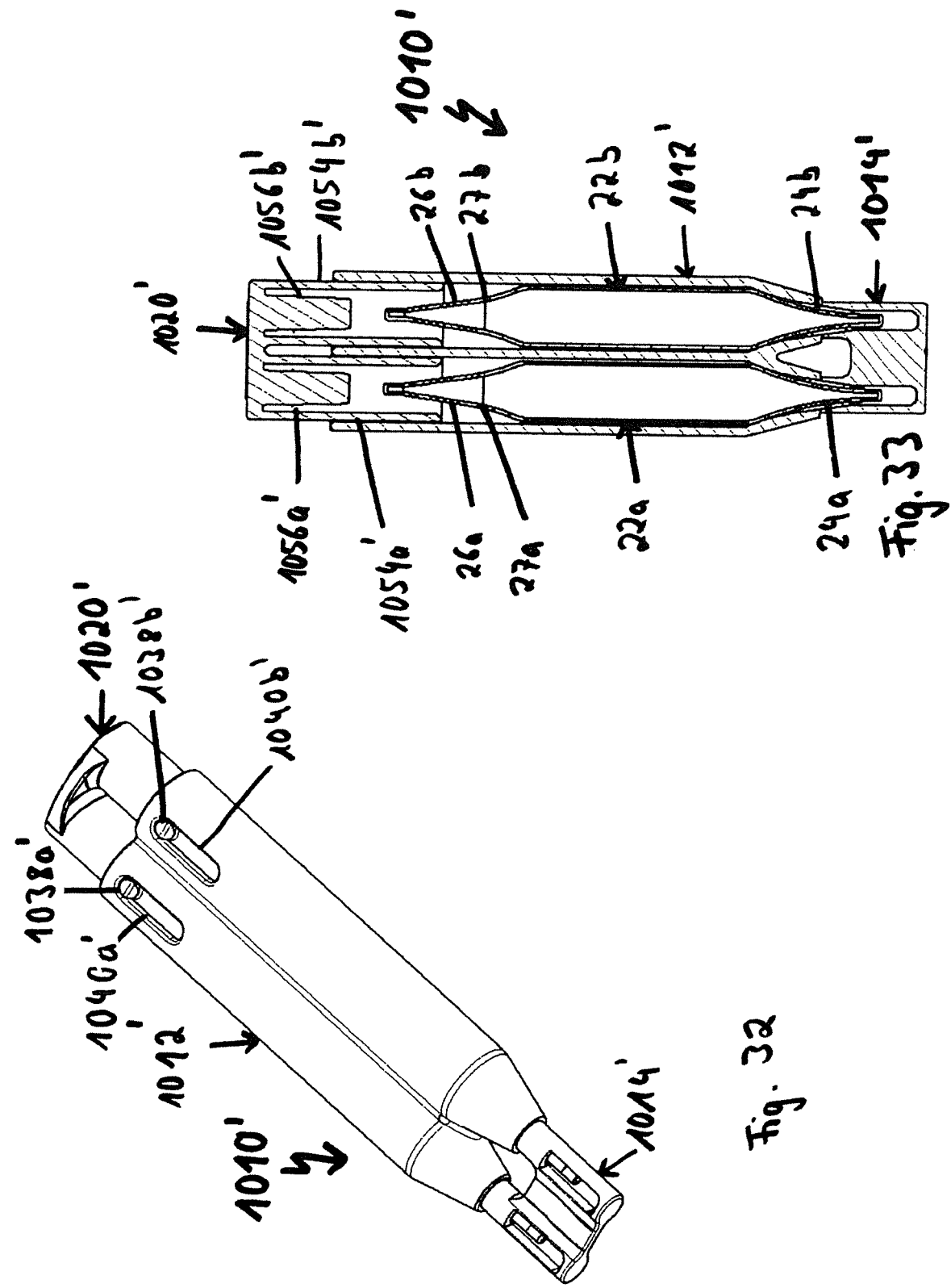

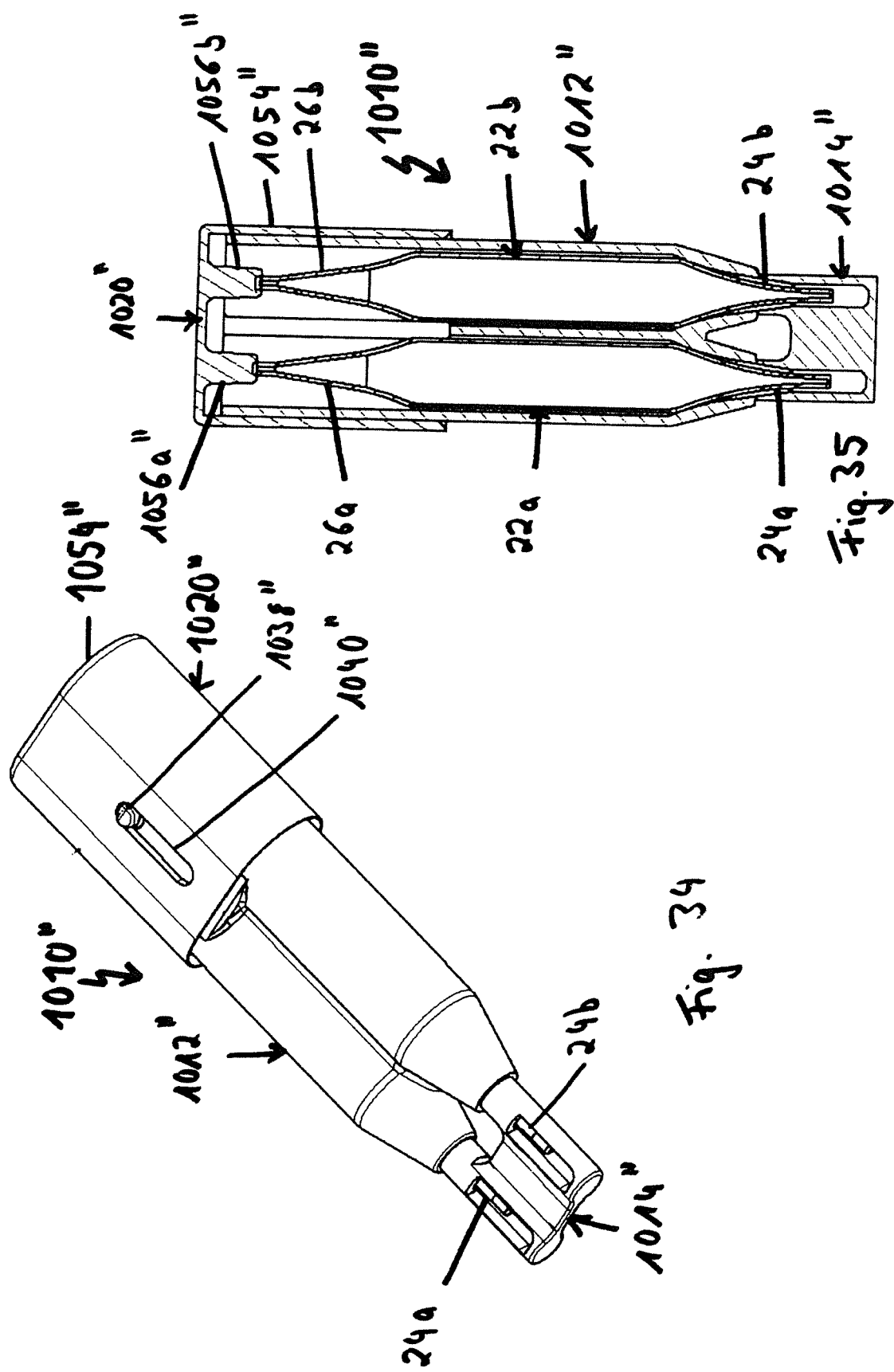

DEVICE FOR DISCHARGING A POURABLE SUBSTANCE

This application represents the national stage entry of PCT International Application No. PCT/EP2018/083527 filed Dec. 4, 2018, which claims priority of German Patent Application No. DE 10 2017 128 918.6 filed Dec. 5, 2017 and German Patent Application No. DE 10 2018 115 344.9 filed Jun. 26, 2018. Each of these applications is incorporated herein by reference in their entirety for all purposes.

The disclosure relates to a device for discharging a flowable substance, in particular for applying a medical substance, a pharmaceutical substance, a food supplement or cosmetics.

From practice, a device having an inner sleeve and an outer sleeve is known, in which a frangible capsule is disposed and which is provided with a discharge opening at its front side. A flowable substance, such as a glue, is contained in the capsule. Before applying the flowable substance via the discharge opening, the capsule is broken by means of an inner sleeve acting in the axial direction so that the flowable substance flows through the discharge opening.

The known device does not allow applying or pipetting the flowable substance in a defined manner. Moreover, the capsule is not retained in its position in the device.

The object of the disclosure is therefore to create a device for discharging a flowable substance by means of which a flowable substance, which is initially contained in a frangible capsule, can be applied and discharged in a defined manner and a position of the capsule is retained or determined in the device.

Thus, the disclosure proposes a device having a body, such as an applicator sleeve, for discharging a flowable substance, in particular for applying a medical substance, a pharmaceutical substance, a food supplement or cosmetics. The body has a discharge opening at one end and forms a containing space with a wall space, in which a frangible capsule containing the flowable substance is positioned. At a second end of the body, an activation mechanism is disposed. The capsule has a tip at each of its ends, at least one of the tips being able to be snapped off by actuating the activation mechanism so that the flowable substance can be discharged and applied in a defined manner.

In an expedient embodiment, the capsule is made of glass. Glass has the advantage of being chemically resistant to a number of substances and consequently is particularly suitable for holding medical or pharmaceutical substances.

Alternatively, the capsule can be made of a frangible plastic chemically resistant to the flowable substance.

In a specific embodiment, the capsule has a predetermined breaking point at both of its ends so that each of the two ends can be snapped off the capsule in a defined manner.

In an advantageous embodiment, the capsule is positioned or retained in its position in the containing space of the body by the activation mechanism, in particular by a protrusion of the activation mechanism and/or by a corresponding design of the body of the device itself. This ensures that the tip(s) of the capsule is/are snapped off correctly and the flowable substance can be discharged via the discharge opening after removal of the tip(s).

In an alternative embodiment, the body has an end section at the first end, the end section being designed as a constriction or a tapering via which the flowable substance can be discharged and applied in a defined manner.

The first tip of the capsule can also be disposed in the end section, whereby the capsule is positioned spatially in the body and a user can snap off the tip without directly touching the tip.

In an advantageous embodiment, the end section is made of an elastic, compressible or frangible material. By deforming, compressing or breaking the end section, the tip of the capsule disposed in the end section is snapped off so that the flowable substance contained in the capsule can be applied drop by drop and in a defined manner.

The end section can be a tipping lock or a Luer lock and/or form a spoon at the end facing away from the body. Furthermore, the end section can have grip elements, whereby a user can easily remove the end section and thus the first tip.

In an alternative embodiment, an applicator made of absorbent material is disposed at the discharge opening. The applicator sucks up or absorbs the substance flowing from the capsule after the device has been activated or at least one tip of the capsule has been removed. Thus, the flowable substance can be applied on the other side of the applicator in a defined manner.

In particular on the discharge side, the shape of the applicator can be adjusted to a respective area of use, whereby user friendliness is enhanced.

The activation mechanism is, for example, a piston, a vacuum chamber or consists of a flexible material, such as a rubber cap.

In particular when an activation mechanism is designed as a piston, the activation mechanism can have a bevel or a beveled edge on a side facing the capsule so that a force is exerted on the tip of the capsule in such a manner when axially displacing the activation mechanism that the second tip snaps off in a defined manner, meaning the risk of damaging the capsule is reduced.

If the activation mechanism consists of the flexible material, it can then be connected to the body or the applicator sleeve by means of a retaining element. For this purpose, the retaining element has teeth, for example, which can engage into corresponding recesses and lock there, or it has a thread which is engaged with a corresponding counter thread formed on the body.

In an advantageous embodiment, the activation mechanism is actuated by being axially displaced, bent or compressed so that the second tip or the first and the second tip of the capsule are snapped off and the flowable substance of the capsule can be applied or discharged.

In particular the first and the second tip of the capsule can be snapped off upon the axial displacement of such an activation mechanism realized as a piston, for example, so that the device can be actuated with one hand.

In an alternative embodiment, the body has a ramp which contacts the piston when the activation mechanism is actuated. This limits a relative movement of the piston with respect to the body so that the capsule will not be damaged by the piston.

Preferably, the ramp is formed at the wall area of the body or at the second end of the body.

In an advantageous embodiment, the activation mechanism has a peg and the body has a slit corresponding to the peg. The peg of the activation mechanism is positioned in the slit of the body, whereby a displacement path or rotation path of the piston is limited with respect to the body.

This ensures in a simple manner that the second tip of the capsule snaps off while a capsule body remains intact when the activation mechanism is actuated.

In a preferred embodiment, a resetting element is disposed between the body and the activation mechanism and (re)sets the activation mechanism into its original position after being actuated. This enables performing a pumping movement for discharging the flowable substance in particular if the activation mechanism is a piston.

Preferably, a holding aid is disposed on the body or is formed by the body, thus increasing user friendliness.

In an alternative embodiment, the body comprises a deformed area by means of which the flowable substance can be discharged and applied in a defined manner.

In an advantageous embodiment, the body is a tube and the activation mechanism is a seal, in particular a welding seal, which is disposed at the end of the body facing away from the discharge opening. The second tip of the capsule or a part thereof is located in the seam so that the second tip of the capsule snaps off when actuating the activation mechanism, in particular by bending the seam, without a user having to come into contact with the capsule itself.

At the front end of the tube, a folded seal can be disposed in which the first tip of the capsule is located so that the first tip of the capsule also snaps off when the folding seal is snapped off.

In particular, the seal or the welding seal is designed such that the user sees a generic tube.

The tube can also be made of a rigid material so that it cannot be deformed.

In an advantageous embodiment, the activation mechanism is provided with a marking, such as a written character, to indicate correct mode of activation to the user.

In an alternative embodiment, the body forms two or more containing spaces in each of which a capsule is disposed so that several tips of capsules can be snapped off at the same time by actuating an activation mechanism and thus several flowable substances can be applied simultaneously, without these substances being mixed or blended beforehand.

Exemplary embodiments of a device according to the disclosure are illustrated in the drawing in a schematically simplified manner and are described in further detail in the following description. In the drawing, FIG. 1 is a perspective view of a capsule disposed in the device according to the disclosure;

FIG. 3 is a perspective view of an alternative embodiment of the device according to FIG. 2;

FIG. 4 is a lateral view of an alternative embodiment of the device according to FIG. 2;

FIG. 5 is a lateral view of an alternative embodiment of the device according to FIG. 4;

FIG. 6 is a perspective view of an alternative embodiment of the device according to FIG. 2;

FIG. 7 is a sectional view through the device according to FIG. 6;

FIG. 8 is a perspective view of an alternative embodiment of a device according to the disclosure;

FIG. 9 is a sectional view through the device according to FIG. 8;

FIG. 10 is a perspective view of an alternative embodiment of the device according to FIG. 8;

FIG. 11 is a perspective view of an alternative embodiment of the device according to FIG. 8;

FIG. 12 is a sectional view through the device according to FIG. 11;

FIG. 13 is a perspective view of an alternative embodiment of the device according to FIG. 8;

FIG. 14 is a sectional view through the device according to FIG. 13;

FIG. 15 is a perspective view of an alternative embodiment of a device according to the invent-disclosure;

FIG. 17 is a lateral view of an alternative embodiment of a device according to the disclosure;

FIG. 18 is a lateral view of an alternative embodiment of the device according to FIG. 18;

FIG. 19 is a lateral view of an alternative embodiment of a device according to the disclosure;

FIG. 23 is a perspective view of an alternative embodiment of a device according to the disclosure;

FIG. 24 is a lateral view of the device according to FIG. 23;

FIG. 25 is a sectional view through the device according to FIG. 23 along line XXIV-XXIV in FIG. 24.

FIG. 26a is a perspective view of an alternative embodiment of a device according to the disclosure;

FIG. 26b is a perspective view of an alternative embodiment of the device according to FIG. 26a;

FIG. 27 is a sectional view through the device according to FIG. 26a;

FIG. 30 is a perspective view of an alternative embodiment of a device according to the disclosure;

FIG. 31 is a sectional view through the device according to FIG. 30;

FIG. 32 is a perspective view of an alternative embodiment of the device according to FIG. 30;

FIG. 33 is a sectional view through the device according to FIG. 32;

FIG. 34 is a perspective view of an alternative embodiment of the device according to FIG. 30;

FIG. 35 is a sectional view through the device according to FIG. 34.

Figure 1:
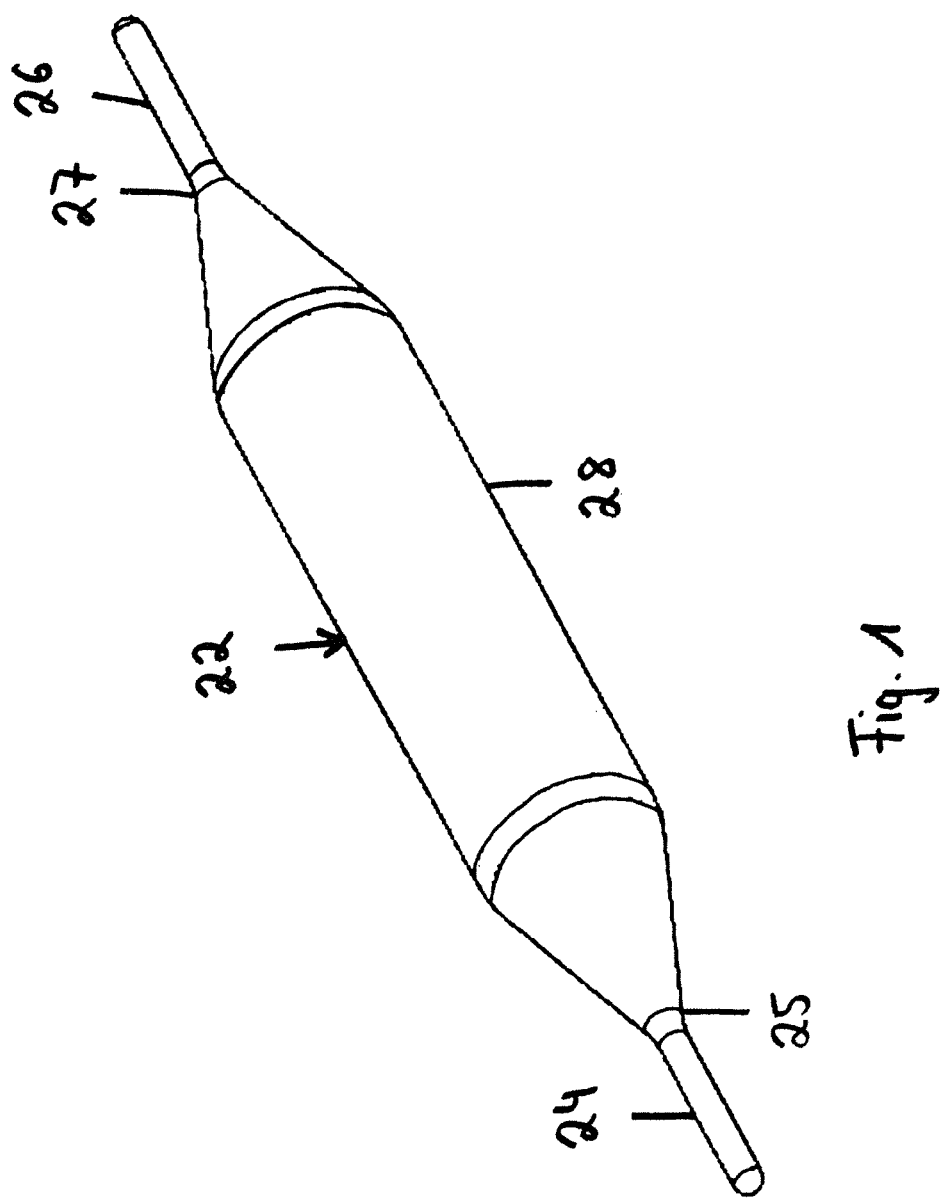

FIG. 1 shows a capsule 22 which contains a flowable substance, in particular a medical substance, a pharmaceutical substance, a food supplement or cosmetics. Capsule 22 has a main body 28 which tapers to a first tip 24 and a second tip 26 on both sides. Predetermined breaking points 25 and 27, at which tips 24 and 26 can be snapped off the body, are each located between main body 28 and each tip 24 and 26.

By adjusting an opening diameter of capsule 22 which forms after snapping off tips 24 and 26 at the respective predetermined breaking point 25 or 27 and by adjusting a viscosity of the flowable substance, a flow rate or discharge rate of the flowable substance from the capsule 22 can be controlled. If a tip 24 or 26 of capsule 22 is removed, the flowable substance is discharged drop by drop from capsule 22. By removing both tips 24, 26, the flow rate will increase.

Figure 2:
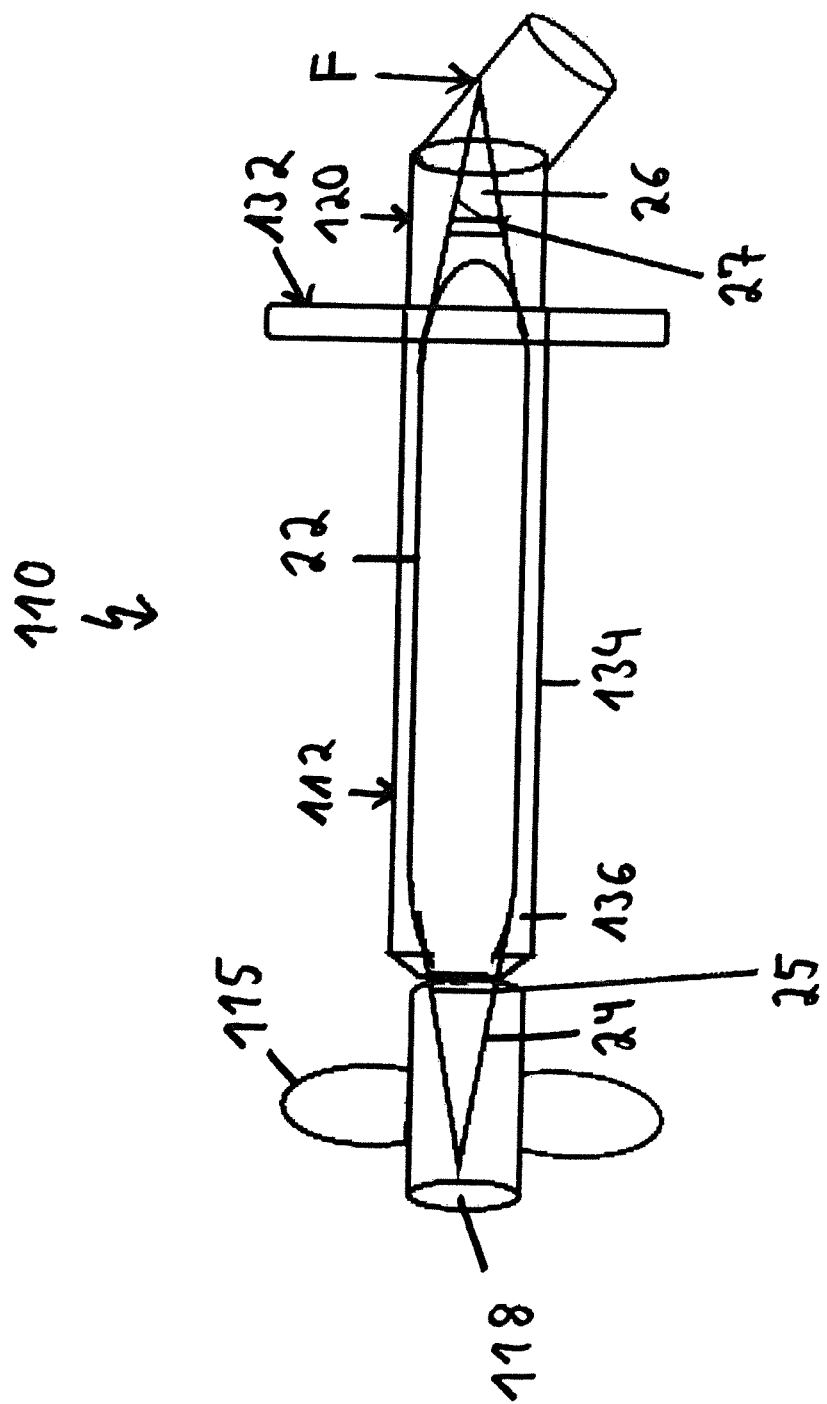
FIG. 2 is a sectional view of a first embodiment of a device according to the disclosure.

FIG. 2 shows a device 110 for applying the flowable substance in an actuation position of an activation mechanism 120. Device 110 has a body and an application sleeve 112 which forms a containing space 136 for capsule 22 together with a wall area 134, and an activation mechanism 120 is disposed at one end of applicator sleeve 112. Activation mechanism 120 is made off a flexible material and fixed to applicator sleeve 112 in such a manner that the second tip 26 of capsule 22 is located therein. Thus, second tip 26 of capsule 22 can be snapped off at predetermined breaking point 27 by actuating or bending activation mechanism 120.

In an area facing away from activation mechanism 120, applicator sleeve 112 tapers to an end section 114 with a discharge opening 118 and grip elements 115. End section 114 receives tip 24 of capsule 22 so that a user can snap off first tip 24 of capsule 22, without coming into direct contact with first tip 24.

At an end area of applicator sleeve 112 facing activation mechanism 120, device 110 has a holding aid 132, which enables easy usage of the device.

Activation mechanism 120 can be a vacuum chamber, whereby a negative pressure presides in activation mechanism 120. This enables being able to apply the flowable substance contained in capsule 22 on an intended area in a defined manner after removing both tips 24 and 26. Device 110 acts as a generic drug pipette and an uncontrolled outpouring of the flowable substance is prevented.

If activation mechanism 120 is fixed to applicator sleeve 112 without any particular precautions regarding the presiding pressure, the substance contained in capsule 22 flows or spurts out of capsule 22 at a comparatively high rate after removing both tips 24 and 26.

Activation mechanism 120 can be provided with a marking or a usage note which indicates correct mode of use of activation mechanism 120.

FIG. 3 shows an alternative embodiment of device 110' in the scope of device 110 shown in FIG. 2 according to the disclosure; markings, which are not further described, correspond to the markings of device 110 of FIG. 2.

Device 110' has an applicator sleeve 112' similar in shape to capsule 22, with the exception that the wall thickness becomes thicker in an area facing activation mechanism 120'. By enlarging the wall thickness, applicator sleeve 112' forms a holding aid 132' with a recess 182' comprising a lid surface 172'.

Moreover, device 110' comprises a fixing element 148' having teeth 186' which correspond to recesses 182' of lid surface 172' and engages them when assembling or mounting device 110'. Thus, teeth 186' are fixed in recesses 182' and activation mechanism 120' is fixed to applicator sleeve 112'.

FIG. 4 shows a second alternative embodiment of a device 110" in the scope of device 110 shown in FIG. 2 according to the disclosure, device 110" differing from the previously shown embodiments in that a fixing element 148" is retained on an applicator sleeve 112" by means of a thread and fixing element 148" has a holding aid 132".

Holding aid 132" is tied to fixing element 148" and extends along an activation mechanism 120", the distance from holding aid 132" to activation mechanism 120" increasing starting at fixing element 148".

Holding aid 132" is shaped such that it is comfortable to hold for a user. For this purpose, edges of holding aid 132", which are on a side facing the user's hand, are rounded.

FIG. 5 shows a further alternative embodiment of a device 110''' according to the disclosure in the scope of device 110 shown in FIG. 2, device 110''' differing from device 110 shown in FIG. 2 in that an activation mechanism 120''' is bound to an applicator sleeve 112''' and that a holding aid 132''' is designed differently. The other features correspond to the features of device 110.

Activation mechanism 120''' has a flange 121''' at an end facing application sleeve 112''', activation mechanism 120''' being fixed to application sleeve 112''' via a fixing element 148''' comprising a thread by means of flange 121'''. Fixing element 148''' comprises holding aid 132'''.

FIGS. 6 and 7 show another alternative embodiment of device 110'''' according to FIG. 2; features not further described in the following automatically correspond to the features of device 110 shown in FIG. 2.

Device 110'''' comprises an applicator sleeve 112'''' having a front body 115'''' and a back main body 116''''. Front main body 115'''' comprises an end section 114'''' at an end facing first tip 24 of capsule 22. End section 114'''' can be snapped off, first tip 24 of capsule 22 also being snapped off when snapping off end section 114'''' so that the flowable substance contained in the capsule can be applied.

Back main body 116'''' has an activation mechanism 120'''', which is designed like a lever, at an end facing second tip 26 of capsule 22. Activation mechanism 120'''' is made of a flexible material so that second tip 26 of capsule 22 is snapped off when actuating activation mechanism 120'''', i.e., when a force which acts in the radial direction of device 110'''' is exerted on activation mechanism 120''''. Moreover, applying or pipetting the flowable substance in a defined manner is possible owing to the flexible material of activation mechanism 120''''.

A holding aid 132'''' is disposed in the shape of a flat surface on a side of the back main body 116'''' opposite to activation mechanism 120'''' in the circumferential direction.

FIGS. 8 and 9 show an alternative embodiment of a device 210 according to the disclosure.

Device 210 has an applicator sleeve 212, which contains a capsule 22 and tapers from a cylindrical main body 216 to an end section 214 in an area facing away from an activation mechanism 220, and activation mechanism 220.

As FIG. 9 shows, activation mechanism 220 is a piston which has a linear bevel 231 acting asymmetrical to tip 26 of capsule 22. By means of bevel 231, second tip 26 of capsule 22 can be snapped off at predetermined breaking point 27 in an optimized manner.

Applicator sleeve 212 has a holding aid 232 made up of two opposite protrusionting elements 232a, 232b which enable a user to pick up device 210 with two fingers, in particular their ring and index finger, in such a manner that that activation mechanism 220 can be actuated by the palm of the hand or the thumb, whereby the activation mechanism 220 can be displaced into applicator sleeve 212 in the axial direction and second tip 26 of capsule 22 is snapped off indirectly.

A slit 240 extending in the axial direction is formed on applicator sleeve 212. Activation mechanism 220 has a peg 238 corresponding to slit 240 of applicator sleeve 212 and disposed therein. Thus, a trajectory of peg 238 and consequently a movement play of activation mechanism 220 can be defined and limited relative to applicator sleeve 212 by slit 240.

By means of peg 238 and slit 240, it can consequently be ensured that activation mechanism 220 is only displaced as far in the direction of capsule 22, i.e., in the axial direction, upon actuation that second tip 26 is snapped off while a risk of damaging main body 28 of capsule 22, however, is precluded.

Owing to actuating the activation mechanism 220 in such a manner and snapping off end section 214, the flowable substance contained in capsule 22 can be applied.

FIG. 10 shows an alternative embodiment of a device 210', in particular a design of an applicator sleeve 212' and a holding aid 232' of device 210 illustrated in FIGS. 8 and 9. All other features of device 210' correspond to device 210 shown in FIGS. 8 and 9.

Applicator sleeve 212' has a front main-body section 215' and a back main-body section 216'. Front main-body section 215' is cylindrical and tapers to an end section 214'. Front main-body section 216' is also cylindrical in an area facing activation mechanism 220'. In an area facing front main-body section 215', the diameter of the cylindrical back main-body section 216' becomes enlarged, the thickness of a wall area 234', which forms applicator sleeve 212', being constant. Back main-body section 216' approximately ends in the middle area of capsule 22. Front main-body section 215' extends toward back main-body section 216' and toward activation mechanism 220' until it comes into contact with back main-body section 216'. Therefore, the diameter of back main-body section 216' is larger in a middle area of applicator sleeve 212' than that of front mainbody section 215', both main-body sections 215' and 216' being connected by fins 250'.

The rise of applicator sleeve 212' resulting from the enlarged diameter of back mainbody section 216' forms holding aid 232', fins 250' stabilizing holding aid 232'.

The embodiment of a device 210'' shown in FIGS. 11 and 12 differs from device 210 shown in FIGS. 8 and 9 in that an applicator sleeve 212'' and a holding aid 232'' are shaped differently and in that a resetting element 248'', which resets an activation mechanism 220'' into its original position after having been axially displaced toward an end section 214'', is disposed between applicator sleeve 212'' and activation mechanism 220''.

The integration of such a resetting element 248'' into other embodiments is also conceivable.

FIGS. 13 and 14 show an alternative embodiment of a device 210''' to device 210 shown in FIGS. 8 and 9; only the features of device 210''' which deviate from those of device 210 will be described in further detail in the following.

Device 210''' comprises a holding aid 232''' disposed at the end facing second tip 26 of capsule 22 and an activation mechanism 220'''. Activation mechanism 220''' is a piston which has a linear bevel 231''' acting asymmetrically on tip 26 of capsule 22. Second tip 26 of capsule 22 can be snapped off at predetermined breaking point 27 in an optimized manner by means of bevel 231'''.

Figure 16:
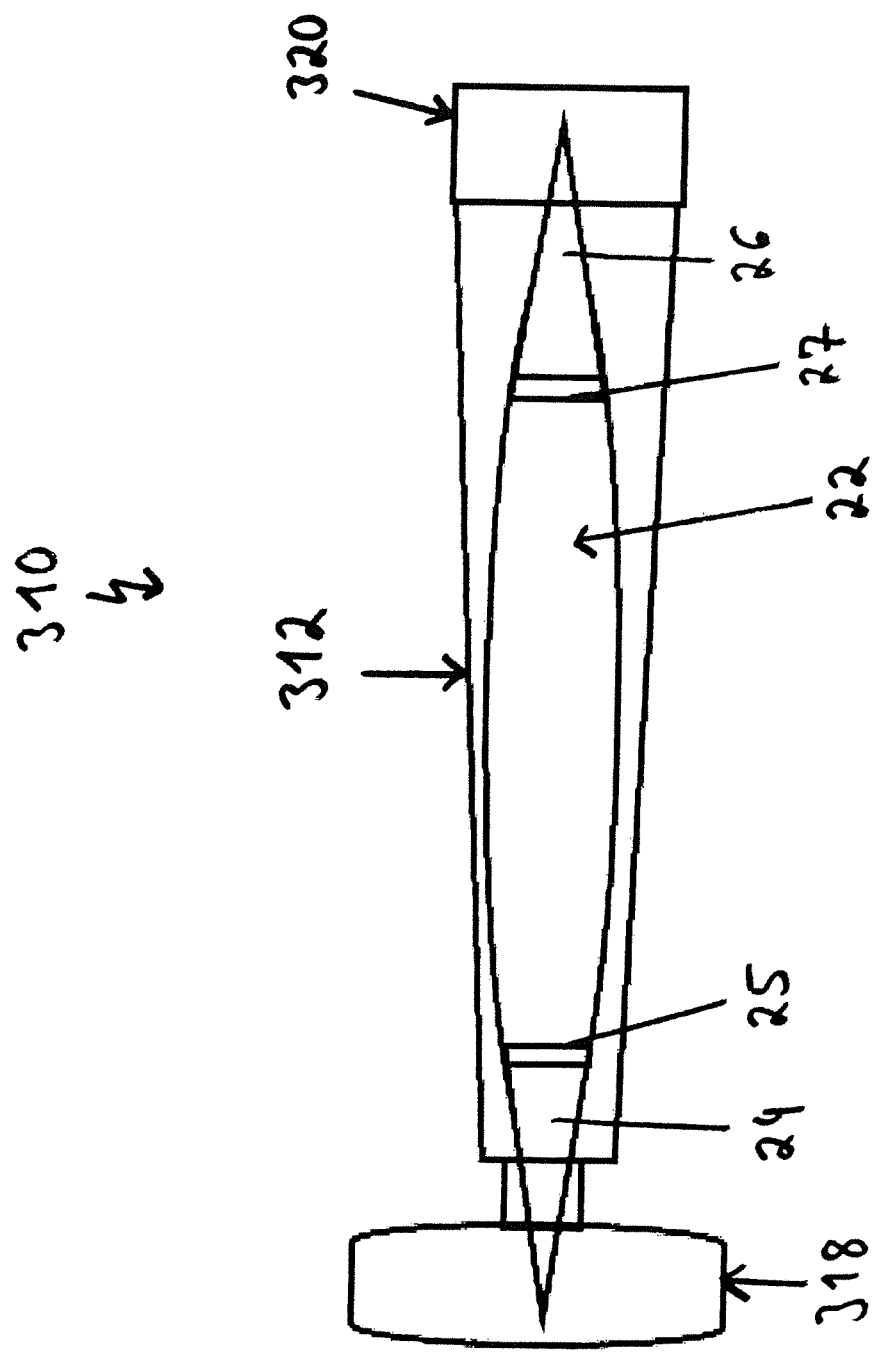
FIG. 16 is a sectional view through an alternative embodiment of the device according to FIG. 15.

A further alternative embodiment of a device 310 according to the disclosure is shown in FIGS. 15 and 16. Device 310 comprises a rigid tube 312 which contains capsule 22. Tube 312 has a cap 318 at one end and a welding seal 320 serving as an activation mechanism at the other end. Cap 318 is a bend-off cap and can comprise grip elements.

Before assembling device 310, tube 312 has an opening on a side which faces away from cap 318 and through which capsule 22 is inserted into tube 312 so that capsule body 28 and first tip 24 of capsule 22 are located in tube 312 and an end section of second tip 26 or second tip 26 is located in the opening of tube 312. The opening of tube 312 is subsequently sealed, in particular welded, so that second tip 26 is integrated into welding seal 320 or in a weld surface.

Welding seal 320 is flexible and deformable. Thus, second tip 26 of capsule 22 can be snapped off by bending welding seal 320. By subsequently removing first tip 24 of capsule 22, the flowable substance can consequently be applied.

FIG. 17 shows an alternative embodiment of a device 410 according to the disclosure.

Device 410 comprises an applicator sleeve 412 containing capsule 22 and an applicator 418. Applicator sleeve 412 can be deformed in an area facing applicator 418 and in an end section facing away from applicator 418, whereby both tips 24 and 26 of capsule 22 can be snapped off. Actual applicator sleeve 412 is consequently an activation mechanism.

Applicator 418 is made of an absorbent material. The absorbent material absorbs the flowable substance on the side facing applicator sleeve 412 after both tips 24 and 26 have been snapped off and subsequently discharges the substance on the opposite side in a defined manner.

The embodiment of a device 410' shown in FIG. 18 differs from device 410 illustrated in FIG. 17 in that first tip 24 of capsule 22 is snapped off in an area facing applicator 418' by compressing an applicator sleeve 412'. For this purpose, device 410' has an asymmetric collar 452' which snaps off first tip 24 when axially displacing capsule 22 toward applicator 418'. Device 410' further comprises a protective cap 419'.

FIG. 19 shows a further alternative embodiment of a device 510 according to the disclosure.

Device 510 has an applicator sleeve 512 containing capsule 22. The position of capsule 22 in applicator sleeve 512 is defined by means of a protrusion 590 on the inner side of applicator sleeve 512 and by means of an eccentrically disposed protrusion 592 of an activation mechanism 520 realized as a piston. By axially displacing activation mechanism 520 toward an end section 514, first tip 24 of capsule 22 is snapped off via protrusion 590 and second tip 26 of capsule 22 is snapped off via protrusion 592. End section 514 is disposed on a side facing away from activation mechanism 520 and has an opening 518.

Figure 21:
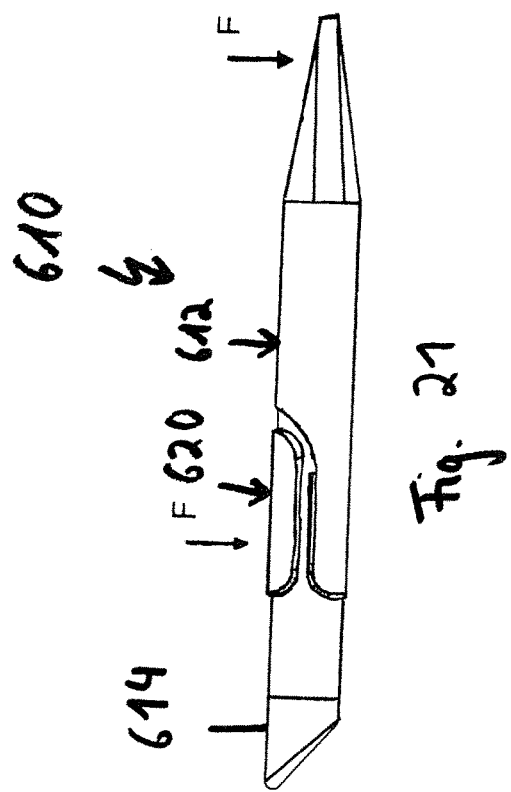
FIG. 21 is a lateral view of the disclosure according to FIG. 20.
Figure 22:
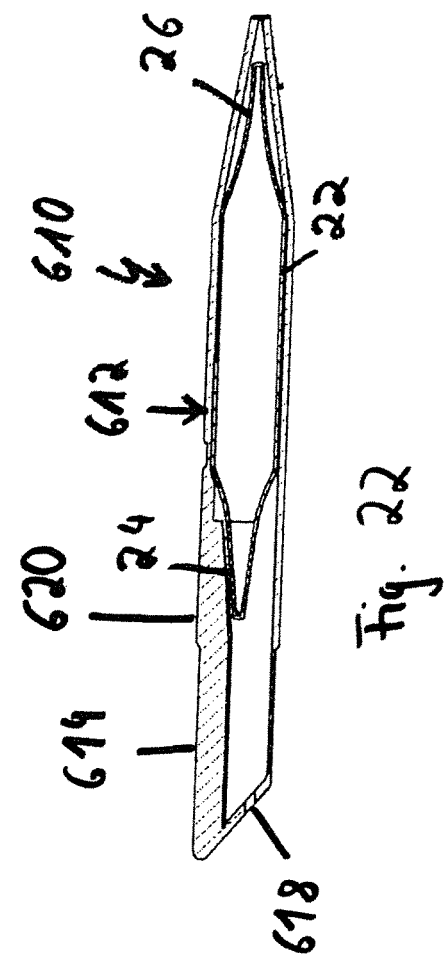
FIG. 22 is a sectional view through the device according to FIG. 20.
Figure 20:
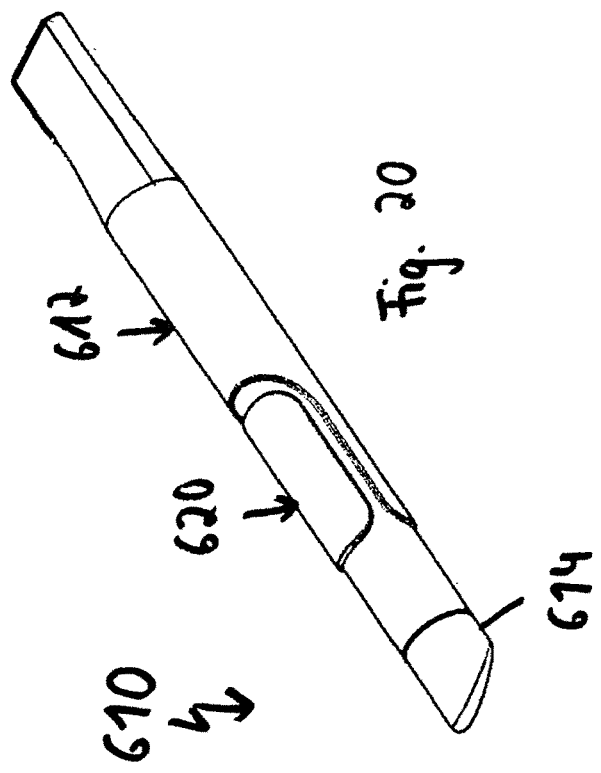
FIG. 20 is a perspective view of an alternative embodiment of a device according to the disclosure.

FIGS. 20 to 22 show a further alternative embodiment of a device 610 according to the disclosure.

Device 610 has an applicator sleeve 612 having an end section 614 comprising a discharge opening 618 and an activation mechanism 620. Activation mechanism 620 is disposed on a level with first tip 24 of capsule 22 and can be actuated by being moved in the radial direction, first tip 24 of capsule 22 being snapped off when actuating activation mechanism 620. Applicator sleeve 612 is made of an elastic material on the side facing end section 614. Thus, second tip 26 of capsule 22 can be snapped off by bending the elastic part of applicator sleeve 612. A defined amount of the flowable substance contained in capsule 22 is applied via discharge opening 618 by actuating activation mechanism 620.

A further embodiment of a device 710 according to the disclosure is shown in FIGS. 23 to 25. Device 710 has an applicator sleeve 712 having an end section 714 and an activation mechanism 720 which is rotatable about the longitudinal axis of device 710 relative to applicator sleeve 712. Capsule 22 is disposed in device 710, in particular applicator sleeve 712 and activation mechanism 720. A first tip 24 of capsule 22 is positioned by means of a positioning element 790 of applicator sleeve 712. Activation mechanism 720 also has a positioning element 792 which secures second tip 26 of capsule 22.

By securing capsule 22 by means of positioning elements 790 and 792, first and second tip 24 and 26 snap off when activation mechanism 720 is rotated so that the flowable substance contained in capsule 22 can be applied via the discharge opening. The rotational leeway of activation mechanism 720 around the longitudinal device axis relative to applicator sleeve 712 is limited by a slit 740 provided in applicator sleeve 714 and a peg formed on activation mechanism 720.

Alternatively, device 710 can be designed without peg 738 and 740 so that rotating activation mechanism relative to applicator sleeve 712 is possible without limitations.

FIGS. 26a, 26b and 27 show a further embodiment of a device 810 according to the disclosure. Device 810 has an applicator sleeve 812 which comprises an activation mechanism 820 in the form of an elastic area in an upper section in the radial direction and a middle section in the axial direction.

Applicator sleeve 812 has an end section 814 at its front end. End section 814 can comprise a spoon-shaped receiving container 815 shown in FIG. 26b. At its back end, applicator sleeve 812 has an opening in which a positioning device 894 is located.

Positioning device 894 extends toward end section 814 and has two positioning elements 890 and 892 by means of which capsule 22 is retained in its position in device 810 via its two tips 24 and 26.

By actuating activation mechanism 820, i.e., by exerting pressure on the elastic area of applicator sleeve 812 in the radial direction, main body 28 of capsule 22 experiences a strain in the radial direction so that both tips 24 and 26 of capsule 22, which are retained in their position, are snapped off, and the flowable substance flows from capsule 22 and can be applied by means of end section 814.

Applicator sleeve 812 of device 810 can be designed in two pieces having a rigid base body and a flexible lid element. The flexible lid element is fixed to the base body by means of a clip connection, for example, and forms the activation mechanism.

Figure 29:
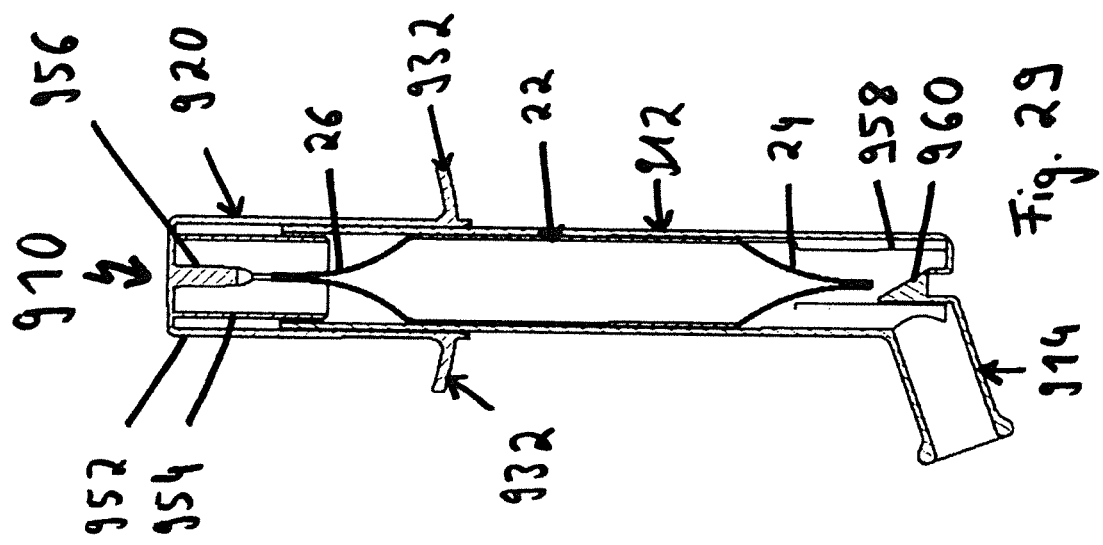
FIG. 29 is a sectional view through the device according to FIG. 28.
Figure 28:
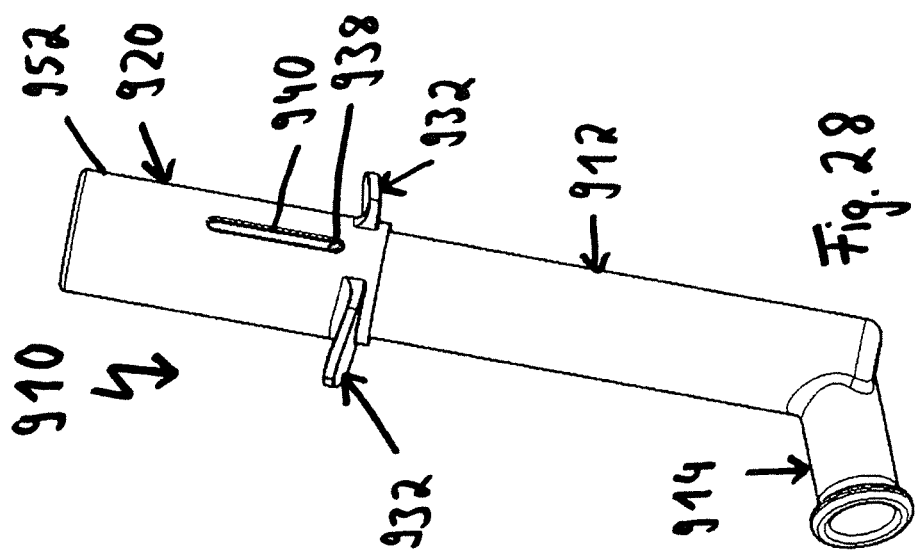
FIG. 28 is a perspective-view of an alternative embodiment of a device according to the disclosure.

A further alternative embodiment of a device 910 according to the disclosure is shown in FIGS. 28 and 29. Device 910 has an applicator sleeve 912 having a holding aid 932 in which capsule 22 is disposed. At one end, applicator sleeve 912 has a positioning element 958 having a bevel 960 and a tube-shaped end section 914 which extends toward a direction opposite to the direction of the axial extension of applicator sleeve 912.

At the other end of applicator sleeve 912, an activation mechanism 920 is disposed which has a cylindric outer wall 952, a cylindric inner wall 954, a slit 940 and an activation element 956. Activation mechanism 920 is mounted in such a manner to applicator sleeve 912 that the wall of applicator sleeve 912 is between outer wall 952 and inner wall 954 of activation mechanism 920. A peg 938, which is formed on applicator sleeve 912 and corresponds to slit 940 of activation mechanism 956, is disposed in slit 940 of activation mechanism 920.

Activation element 956 has a bevel at an end facing capsule 22. By actuating activation mechanism 920, i.e., by displacing activation mechanism 920 toward capsule 22 relative to applicator sleeve 912, second tip 26 of capsule 22 can consequently by snapped off in a defined manner by means of activation element 956 and first tip 24 of capsule 22 can be snapped off by means of bevel 960 of positioning element 958.

FIGS. 30 and 31 show a further alternative embodiment of a device 1010 according to the disclosure.

Device 1010 comprises an applicator sleeve 1012 consisting of two cylindrical parallel partial sleeves which are connected to each other and each receive a capsule 22a or 22b. Applicator sleeve 1012 has a holding aid 1032. At one end of applicator sleeve 1012, an end section 1014 is formed which contains the two first tips 24a and 24b of capsules 22a and 22b. At the other end of applicator sleeve 1012, an activation mechanism 1020 is disposed having two cylindrical partial sleeves 1054a and 1054b, which are connected at an end facing the applicator sleeve by means of lid element 1058. The radius of both partial sleeves 1054a and 1054b are each smaller than the radius of the corresponding partial sleeve of applicator sleeve 1012 so that activation mechanism 1020 can be inserted into or mounted on applicator sleeve 1012. Activation mechanism 1020 has two activation elements 1056a and 1056b on lid element 1058, one of the activation elements 1056a being in first partial sleeve 1054a and the other activation element 1056b being in second partial sleeve 1054b and both activation elements 1056a and 1056b extending toward respective capsules 22a and 22b.

By axially displacing activation mechanism 1020 relative to applicator sleeve 1012, both second tips 26a and 26b of capsules 22a and 22b are snapped off in a defined manner via bevels formed on activation elements 1056a and 1056b.

First tips 24a and 24b of capsule 22a and 22b can be snapped off by bending or snapping off end section 1014 so that after actuating activation mechanism 1020 and snapping off end sections 1014, the flowable substance contained in capsule 22a and 22b can be discharged.

A maximal displacement path of activation mechanism 1020 relative to applicator sleeve 1012 is defined or limited by means of two slits 1040a and 1040b provided on applicator sleeve 1012 and two pegs 1038a and 1038b formed on activation mechanism 1020 and corresponding to slits 1040a and 1040b of applicator sleeve 1012.

An alternative embodiment of device 1010' is shown in FIGS. 32 and 33. Device 1010' illustrated in FIGS. 32 and 33 differs from device 1010 solely in that the capsules contained in device 1010' are of the same size so that the two partial sleeves of applicator sleeve 1012' or the two partial sleeves 1054a' and 1054b' of activation mechanism 1020' correspond to each other. Furthermore, applicator sleeve 1012' does not have a holding aid. All other features correspond to those of device 1010 shown in FIGS. 30 and 31.

FIGS. 34 and 35 show an alternative embodiment of a device 1010" of device 1010' shown in FIGS. 32 and 33, device 1010" differing from device 1010' in that activation mechanism 1020" consists of one sleeve 1054" which is outside of an applicator sleeve 1012". Further features correspond to those of device 1010' shown in FIGS. 32 and 33.

LIST OF REFERENCE NUMERALS 22 capsule
22a capsule
22b capsule
24 first tip
24a first tip
24b first tip
25 first predetermined breaking point
26 second tip
26a second tip
26b second tip
27 second predetermined breaking point
28 main body
110 device
110' device
110" device
110''' device
110'''' device
112 applicator sleeve
112' applicator sleeve
112" applicator sleeve
112''' applicator sleeve
112'''' applicator sleeve
114 end section
114' end section 114'''' end section
115 grip element
115''' front main body
116''' back main body
118 discharge opening
120 activation mechanism
120' activation mechanism
120'' activation mechanism
120''' activation mechanism
120'''' activation mechanism
121''' flange
132 holding aid
132' holding aid
132'' holding aid
132''' holding aid
132'''' holding aid
134 wall area
148' retaining element
148'' retaining element
148''' retaining element
172' lid surface
182' recess
186' teeth
210 device
210' device
210'' device
210''' device
212 applicator sleeve
212' applicator sleeve
212'' applicator sleeve
212''' applicator sleeve
214 end section
214' end section
214'' end section
214''' end section
215' front main-body section
216 main body
216' back main-body section
220 activation mechanism
220' activation mechanism
220'' activation mechanism
220''' activation mechanism
231 bevel
231''' bevel
232 holding aid
232a element
232b element
232' holding aid
232'' holding aid
232''' holding aid
234' wall area
238 peg
240 slit
248'' resetting element
250' fins
310 device
312 tube
318 cap
320 welding seal
410 device
410' device
412 applicator sleeve
412' applicator sleeve
418 applicator
418' applicator
419' protective cap
452' collar
510 device
512 applicator sleeve
514 end section
518 discharge opening
520 activation mechanism
590 protrusion
592 protrusion
610 device
612 applicator sleeve
614 end section
618 discharge opening
620 activation mechanism
710 device
712 applicator sleeve
714 end section
718 discharge opening
720 activation mechanism
738 peg
740 slit
790 positioning element
792 positioning element
810 device
812 applicator sleeve
814 end section
815 spoon-shaped receiving container
818 discharge opening
820 activation mechanism
890 positioning element
892 positioning element
894 positioning element
910 device
912 applicator sleeve
914 end section
920 activation mechanism
932 holding aid
952 outer wall
954 inner wall
956 activation mechanism
958 positioning device
960 bevel
1010 device
1010' device
1010'' device
1012 applicator sleeve
1012' applicator sleeve
1012'' applicator sleeve
1014 end section
1014' end section
1014'' end section
1020 activation mechanism
1020' activation mechanism
1020'' activation mechanism
1032 holding aid
1038a peg
1038b peg
1038a' peg
1038b' peg
1038'' peg
1040a slit
1040b slit
1040a' slit
1040b' slit
1040'' slit
1054a partial sleeve
1054b partial sleeve
1054a' partial sleeve
1054b' partial sleeve 1054" sleeve
1056a activation element
1056b activation element
1056a' activation element
1056b' activation element
1056a" activation element
1056b" activation element
1058 lid element

The invention claimed is:

1. A device for discharging a flowable substance, the device comprising an activation mechanism and a body which has a discharge opening at a first end and forms a containing space in which a frangible capsule is disposed, characterized in that the capsule has two ends each having a first and a second tip and in that at least one of the two tips can be snapped off by actuating the activation mechanism so that the flowable substance is discharged wherein the two ends of the capsule each have a predetermined breaking point for removing the respective tip.

2. The device according to claim 1, wherein the capsule is made of glass.

3. The device according to claim 1, wherein the capsule is positioned in the containing space by the activation mechanism and/or the body.

4. The device according to claim 1, wherein the body has an end section at the first end, the end section being where the first tip of the capsule is disposed.

5. The device according to claim 4, wherein the end section is made of an elastic, frangible or compressible material.

6. The device according to claim 4, wherein the end section is a tipping lock or a Luer lock, the end section has grip elements and/or the end section forms a spoon at an end facing away from the body.

7. The device according to claim 1, wherein an applicator made of an absorbent material is disposed at the discharge opening.

8. The device according to claim 1, wherein the activation mechanism is a piston or is made of a flexible material, or is realized as a vacuum chamber.

9. The device according to claim 8, wherein the activation mechanism is actuated by being axially displaced, bent, rotated and/or exerting pressure in the direction of the capsule.

10. The device according to claim 9, wherein the activation mechanism has a pin which is disposed in a slit corresponding to the pin and formed on the body so that a displacement or rotation path of the activation mechanism is limited relative to the body.

11. The device according to claim 8, wherein a resetting element, which resets the activation mechanism into its initial position after actuation, is realized between the activation mechanism and the body.

12. The device according to claim 1, characterized by a holding aid.

13. The device according to claim 1, wherein the body has an elastic area by which the flowable substance can be discharged from the capsule in a defined manner.

14. The device according to claim 1, wherein the body is a tube.

15. A device for discharging a flowable substance, the device comprising an activation mechanism and a body which has a discharge opening at a first end and forms a containing space in which a frangible capsule is disposed, characterized in that the capsule has two ends each having a first and a second tip and in that at least one of the two tips can be snapped off by actuating the activation mechanism so that the flowable substance is discharged wherein the body is a tube and the activation mechanism is a seam, which is formed on the end facing away from the discharge opening, the second tip or a part of the second tip of the capsule being disposed in the seam and the activation mechanism being actuated by being bent.

16. A device for discharging a flowable substance, the device comprising an activation mechanism and a body which has a discharge opening at a first end and forms a containing space in which a frangible capsule is disposed, characterized in that the capsule has two ends each having a first and a second tip and in that at least one of the two tips can be snapped off by actuating the activation mechanism so that the flowable substance is discharged wherein the body forms at least two containing spaces in each of which one capsule is disposed.

* * * * *